(12) United States Patent
Sauer

(10) Patent No.: US 11,766,326 B2
(45) Date of Patent: Sep. 26, 2023

(54) METHOD OF FOLDING A CARDIAC REPAIR STRUCTURE

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

(*) Notice: Subject to any disclaimer, the term of this patent is extended or adjusted under 35 U.S.C. 154(b) by 0 days.

(21) Appl. No.: 17/179,234

(22) Filed: Feb. 18, 2021

(65) Prior Publication Data

US 2021/0251751 A1 Aug. 19, 2021

Related U.S. Application Data

(60) Provisional application No. 63/090,785, filed on Oct. 13, 2020, provisional application No. 62/978,078, filed on Feb. 18, 2020.

(51) Int. Cl.
*A61F 2/24* (2006.01)

(52) U.S. Cl.
CPC .......... *A61F 2/2418* (2013.01); *A61F 2/2412* (2013.01); *A61F 2/2415* (2013.01); *A61F 2220/0016* (2013.01); *A61F 2250/0023* (2013.01); *A61F 2250/0068* (2013.01)

(58) Field of Classification Search
CPC .................................................. A61F 2/2412
See application file for complete search history.

(56) References Cited

U.S. PATENT DOCUMENTS

| 5,344,442 A * | 9/1994 | Deac ..................... A61F 2/2412 623/901 |
| 5,509,930 A * | 4/1996 | Love ..................... A61F 2/2415 623/900 |
| 5,928,281 A * | 7/1999 | Huynh .................. A61F 2/2412 623/2.14 |
| 6,334,873 B1 * | 1/2002 | Lane ..................... A61F 2/2412 623/2.14 |
| 2002/0052651 A1 * | 5/2002 | Myers .................. A61F 2/2415 623/2.15 |
| 2003/0027332 A1 * | 2/2003 | Lafrance ............. A61L 27/3843 435/366 |

(Continued)

OTHER PUBLICATIONS

International Preliminary Reporton Patentability for International Application No. PCT/US2021/018611 dated Mar. 23, 2022.

*Primary Examiner* — Jacqueline Wozsnicki
(74) *Attorney, Agent, or Firm* — Michael E. Coyne

(57) ABSTRACT

A repair structure apparatus for cardiac surgery is disclosed. The repair structure apparatus includes a fluid reservoir and a platform comprising a porous surface in communication with the fluid reservoir, with a port in communication with the porous surface. The apparatus includes a cutting template configured to align with the platform and a slicing sled configured to engage the platform. A cutting template for constructing a repair structure for cardiac surgery is further disclosed. The cutting template includes a frame having at least one arcuate lobe; and at least one sharpened edge. A device for constructing a repair structure for cardiac surgery is also disclosed, wherein the device includes a porous platform. A repair structure for cardiac surgery is disclosed. The repair structure includes a tissue sheet, wherein the tissue sheet is folded along a free edge of the tissue sheet.

13 Claims, 28 Drawing Sheets

(56) References Cited

U.S. PATENT DOCUMENTS

| | | | |
|---|---|---|---|
| 2003/0114913 A1* | 6/2003 | Spenser | A61F 2/2427 623/2.14 |
| 2003/0130729 A1* | 7/2003 | Paniagua | A61F 2/2412 623/2.14 |
| 2003/0139805 A1* | 7/2003 | Holmberg | A61F 2/2403 623/1.26 |
| 2004/0117009 A1* | 6/2004 | Cali | A61F 2/2412 623/2.12 |
| 2005/0113910 A1* | 5/2005 | Paniagua | A61F 2/2412 623/2.14 |
| 2006/0167542 A1* | 7/2006 | Quintessenza | A61F 2/2412 623/901 |
| 2008/0065198 A1* | 3/2008 | Quintessenza | A61F 2/2475 623/1.24 |
| 2009/0030511 A1* | 1/2009 | Paniagua | A61B 8/12 623/2.13 |
| 2010/0082094 A1* | 4/2010 | Quadri | A61F 2/2403 29/890.132 |
| 2012/0083879 A1* | 4/2012 | Eberhardt | A61F 2/2418 623/2.18 |
| 2012/0310041 A1* | 12/2012 | Paniagua | A61F 2/2418 600/36 |
| 2012/0310335 A1* | 12/2012 | Matheny | A61L 27/3691 623/2.15 |
| 2014/0005766 A1* | 1/2014 | Paniagua | A61F 2/2436 623/2.14 |
| 2014/0163673 A1* | 6/2014 | Bruchman | A61F 2/2415 623/2.42 |
| 2015/0245907 A1* | 9/2015 | Matheny | A61L 27/3633 623/1.26 |
| 2017/0265997 A1* | 9/2017 | Paniagua | A61F 2/2412 |
| 2018/0036120 A1* | 2/2018 | Shin | A61F 2/2412 |
| 2019/0298515 A1* | 10/2019 | Burriesci | A61F 2/2415 |
| 2020/0345495 A1* | 11/2020 | Gammie | A61F 2/2448 |

* cited by examiner

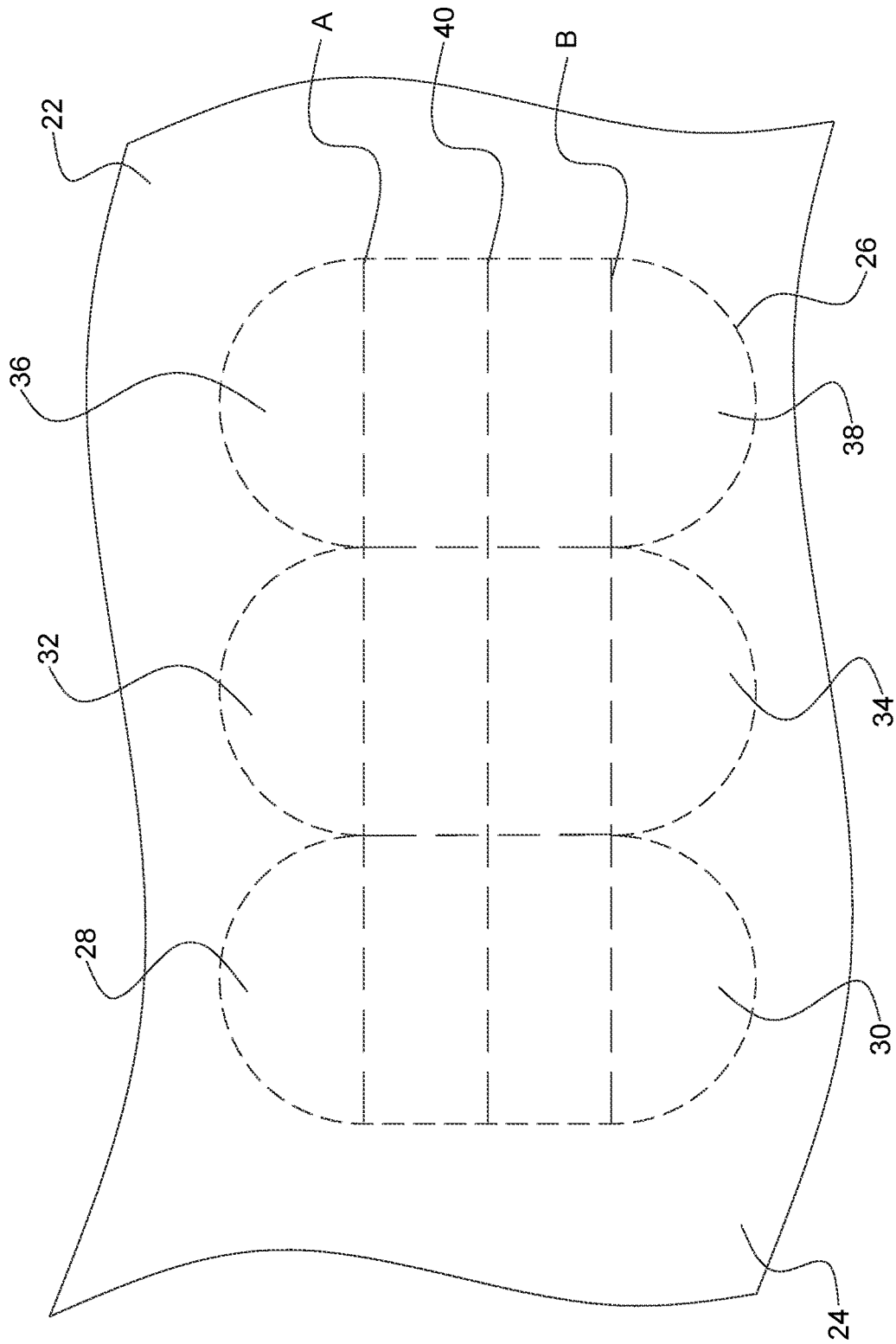

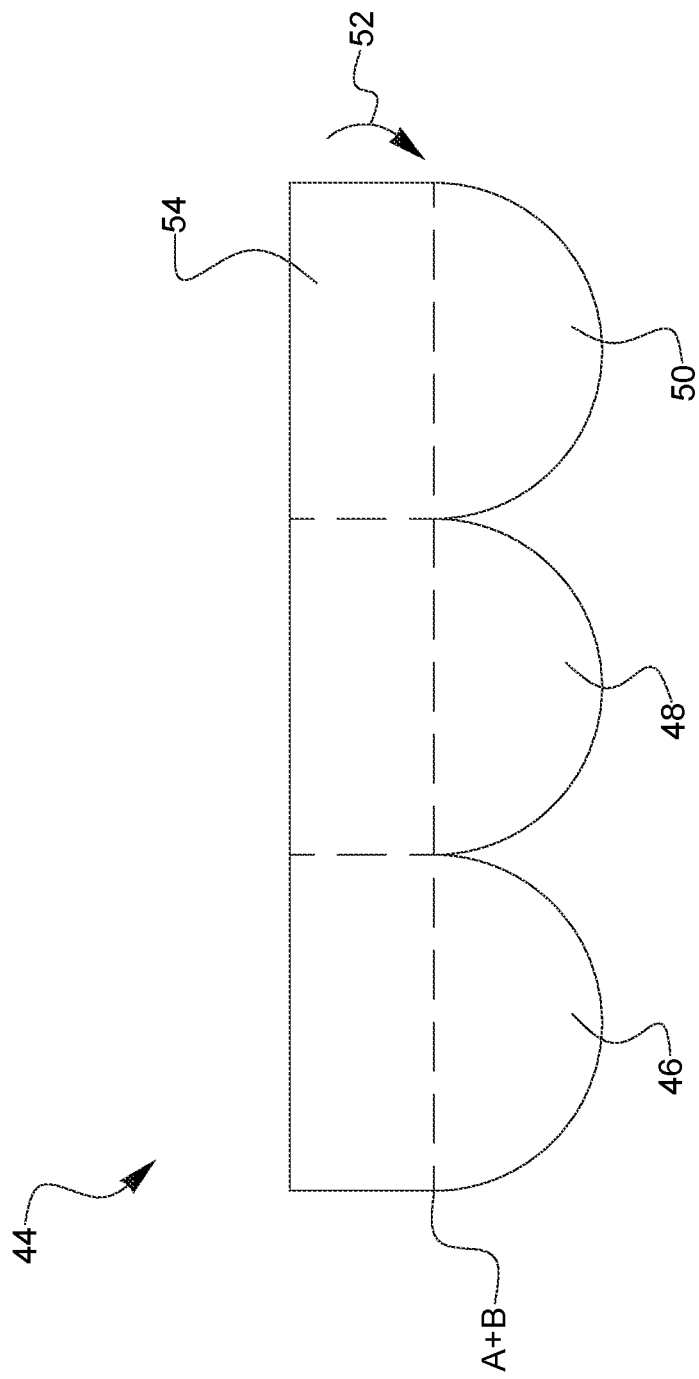

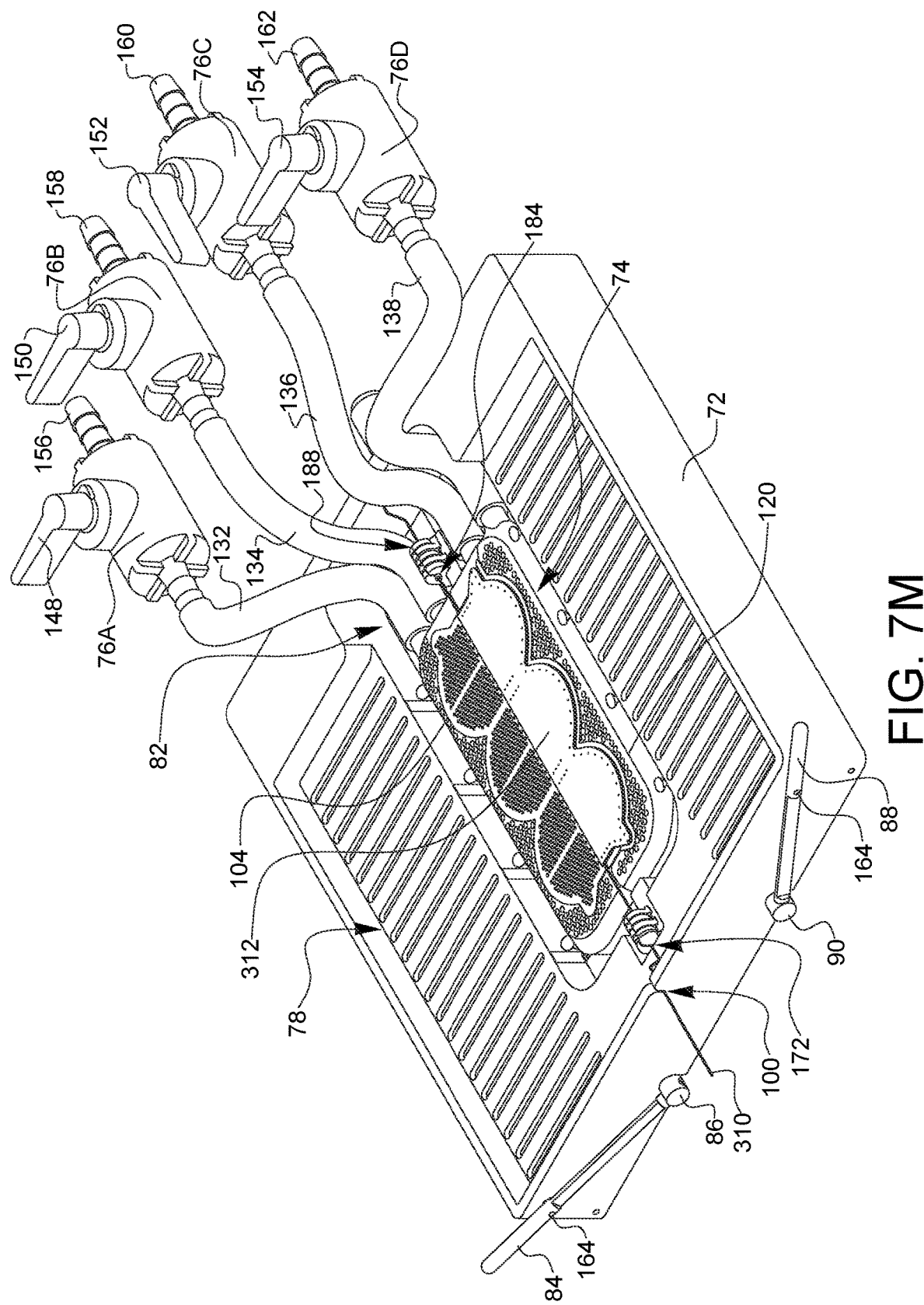

METHOD OF FOLDING A CARDIAC REPAIR STRUCTURE

CROSS-REFERENCE TO RELATED APPLICATIONS

This application claims the benefit of U.S. provisional patent application 62/978,078 entitled CARDIAC REPAIR STRUCTURE filed Feb. 18, 2020 and U.S. provisional patent application 63/090,785 entitled CARDIAC REPAIR STRUCTURE, APPARATUS, AND METHODS THEREOF, filed Oct. 13, 2020, the disclosure of each of which is hereby expressly incorporated by reference.

FIELD

The claimed invention relates to tissue repair structures, and more specifically to a tissue repair structure used during minimally invasive cardiac surgical procedures and a device for constructing the repair structure.

BACKGROUND

The utilization and implementation of preserved and non-preserved autologous tissue for making patches or grafts has several years of precedence in surgical practice. In particular, the Ozaki technique for replacing an aortic valve has realized more acceptance in the field of cardiac surgery during the past decade. One of Dr. Ozaki's advances was to provide templates to enable more precise patterns for cutting preserved autologous pericardial tissue in the shape of leaflets from the patient's own harvested pericardial tissue. This segment of pericardial tissue is cut into three pieces that resemble the shape of the three typical aortic valve leaflets (i.e. left cusp, adjacent to the left coronary artery os, right cusp, next to the right coronary artery and non-coronary cusp) and are cut according to the selected pattern.

Pericardial tissue is harvested from over the anterior surface of the heart, in front of the phrenic nerves on either side. The pericardial surface adjacent to the heart is very smooth while the opposite side often has a rougher surface, typically with collections of attached adipose tissue. A single layer of pericardium is usually sewn into the aortic root with the smooth inside pericardial tissue surface facing the left ventricular side and the rougher outer pericardial surface facing outward towards the wall of the ascending aorta. For the current Ozaki procedure, the harvested pericardial tissue is next preserved by usually a ten minute soaking of 0.6% glutaraldehyde solution followed by a rinsing process. Other tissue preservation techniques and treatment methods are also known, but while these preservation techniques stiffen the tissue, making it easier to handle, they may kill all living tissue cells in the process. Unlike with non-preserved tissue, current preservation techniques provide tissue that may become brittle or degrade over time, and which will not likely grow with growing patients.

There is currently a need for a cardiac repair structure that would last many decades without degradation in the patient. A replacement cardiac valve, for example, would preferably last longer than the duration of the patient's lifespan. In younger patients who are still growing in body and heart size, the ideal replacement valve would also grow with the patient if it was a native tissue based heart valve.

SUMMARY

A repair structure for cardiac surgery is disclosed. The repair structure includes a tissue sheet, wherein the tissue sheet is folded along a free edge of the tissue sheet.

A device for constructing a repair structure for cardiac surgery is also disclosed, wherein the device includes a porous platform.

A cutting template for constructing a repair structure for cardiac surgery is further disclosed. The cutting template includes a frame having at least one arcuate lobe; and at least one sharpened edge.

A repair structure apparatus for cardiac surgery is disclosed. The repair structure apparatus includes a fluid reservoir and a platform comprising a porous surface in communication with the fluid reservoir, with a port in communication with the porous surface. The apparatus includes a cutting template configured to align with the platform and a slicing sled configured to engage the platform.

BRIEF DESCRIPTION OF THE DRAWINGS

FIG. 2A-2C are a series of top views illustrating the construction of the repair structure for cardiac surgery of FIG. 1.

FIGS. 7A-7H, FIGS. 7J-7N, and FIG. 7P-7Q illustrate a method of use for the repair structure apparatus of FIG. 4 and the additional surgical instruments illustrated in FIGS. 6A-6H. It should be noted that FIGS. 7I and 7O have been omitted so as not to be confused with the numerals 71 and 70, respectively.

Figure 1:
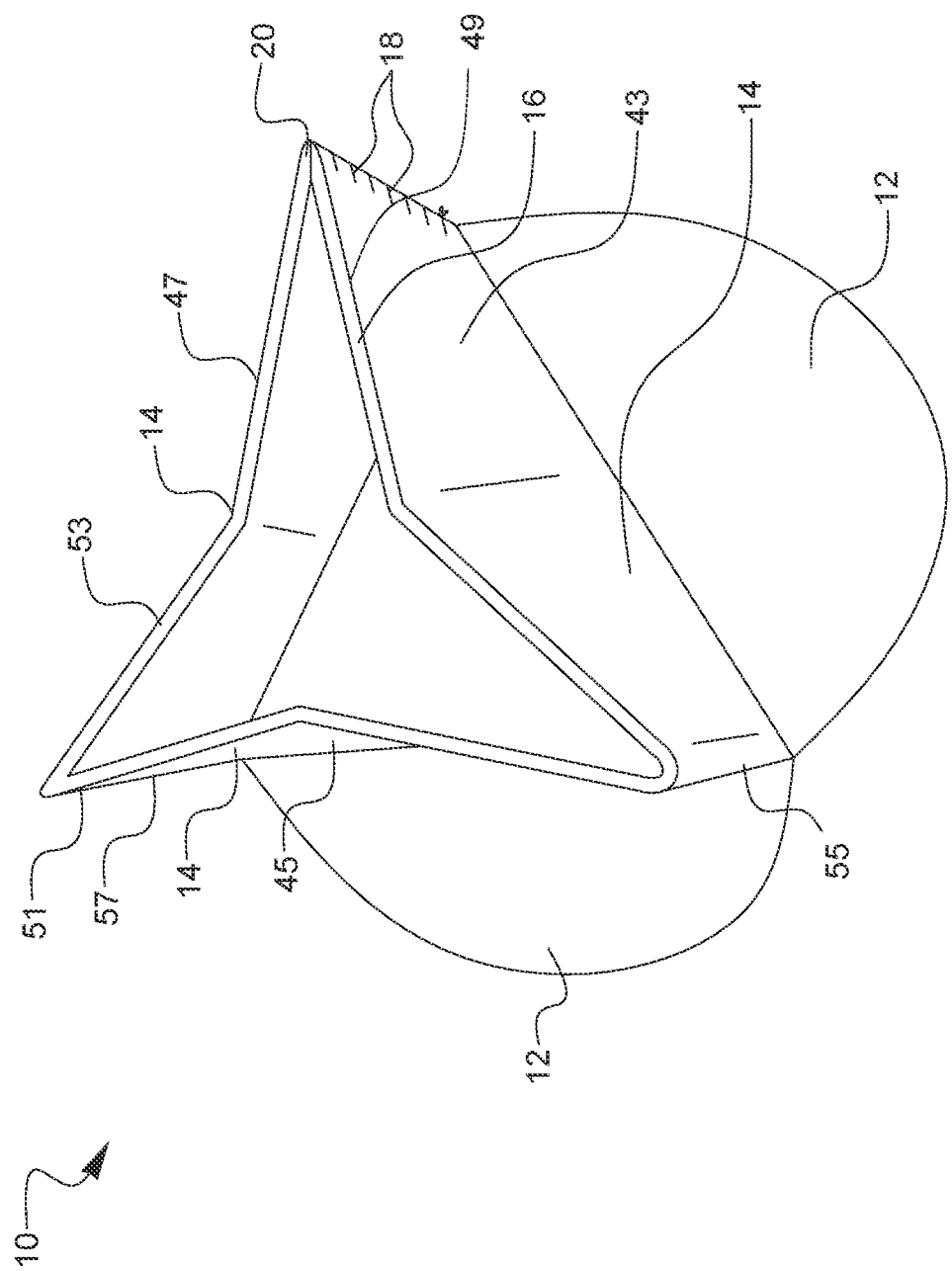
FIG. 1 is a top-left-front perspective view of a repair structure for cardiac surgery.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

FIG. 1 is a top-left-front perspective view of a repair structure for cardiac surgery. The repair structure illustrated is a replacement heart valve constructed of autologous tissue, namely pericardial tissue. The replacement heart valve which is also referred to as a repair structure 10 is structurally robust, made so with the use of two layers of pericardium tissue rather than a single layer for only a single valve leaflet. The embodiment shown in FIG. 1 has several lobes 12 and leaflets 14 and has been folded along a free edge 16. The construction of the repair structure 10 will be further described in regard to FIGS. 2A-2C. The repair structure assembly is completed by sewing the structure at a commissural margin point 20 and an annular margin (not shown here) using a suture 18. The completion of alternate embodiments of repair structures may be accomplished by other means such as tissue welding, biocompatible adhesives, or other means known to those skilled in the art. While this repair structure 10 or replacement valve is constructed from a folded double thickness of pericardial tissue, other embodiments of such a repair structure may include three or more layers of pericardial or other suitable tissue.

Figure 2B:
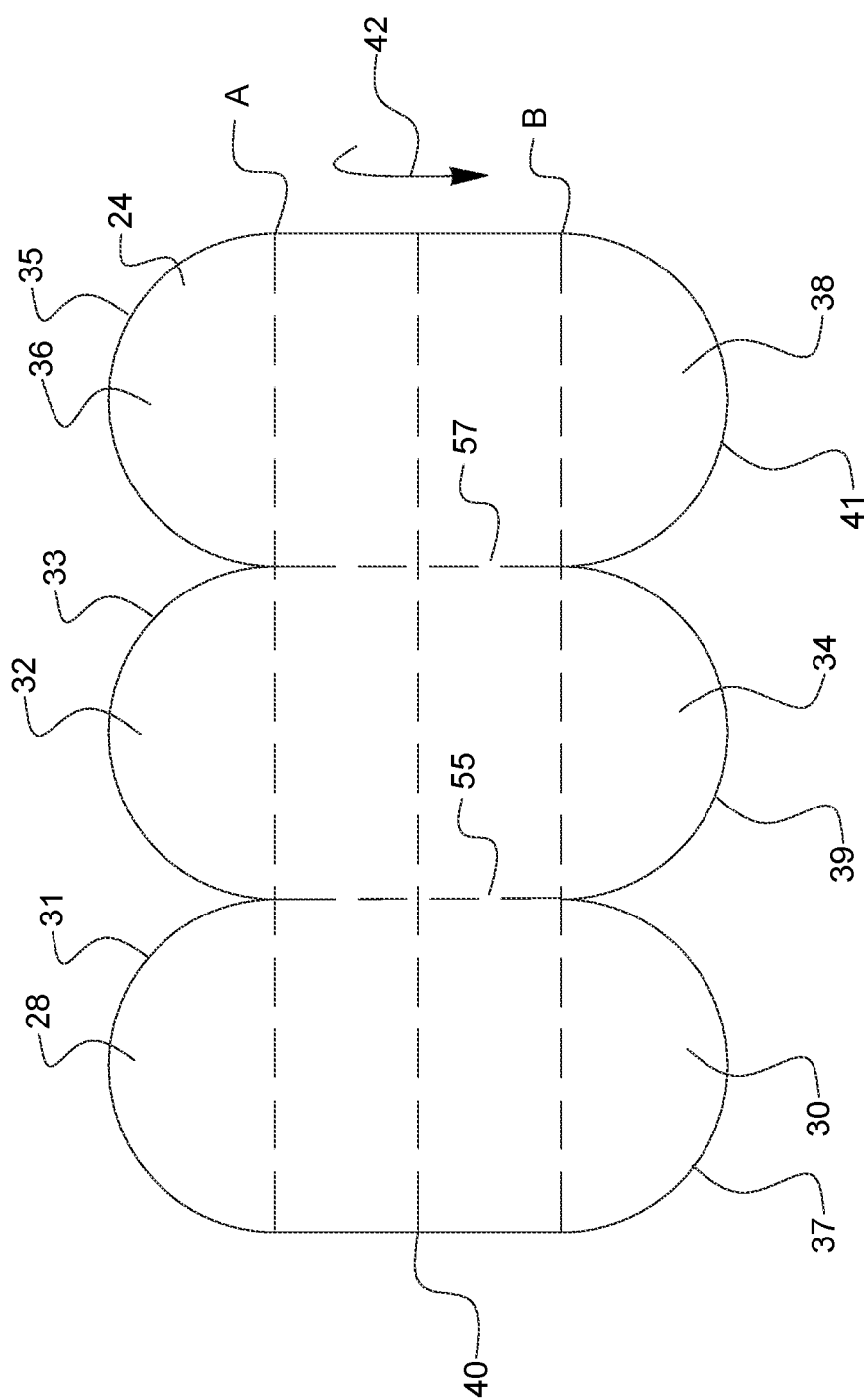

FIG. 2A-2C are a series of top views illustrating the construction of the repair structure for cardiac surgery of FIG. 1. FIG. 2A illustrates a section of harvested pericardial tissue sheet 22 having a rough surface side 24 showing and a smooth surface side on the opposite side, which is not visible in this view. Superimposed upon the pericardial tissue section are several indication lines outlining the first steps of creating the repair structure as described herein. A dissection line 26, shown as a dashed line, outlines a structure having a first portion of a first lobe 28, a second portion of a first lobe 30, first portion of a second lobe 32, a second portion of a second lobe 34, a first portion of a third lobe 36, and a second portion of a third lobe 38. Also indicated on the pericardial tissue section are a folded edge line 40, a lobe line A and a lobe line B. The dissection line 26 indicates the line along with the pericardial tissue 22 will be dissected, first creating the structure which will comprise the repair structure 10 of the present embodiment, in this instance an autologous tissue replacement heart valve.

FIG. 2B illustrates the dissected pericardial tissue, again with a rough side 24 showing and a smooth side on the opposite side. The smooth side is not visible here. Several directional arrows indicate folding directions for the next steps in constructing the autologous tissue replacement heart valve. Along the folded edge line 40, the dissected pericardial tissue is folded in an inward fold direction 42, resulting in the two portions of the rough surface bisected by the folded edge line 40 of the dissected pericardial tissue being folded inward and facing each other. The rougher surface typically possesses collections of attached adipose tissue, which may be a nidus or focal point for thrombosis formation. Lobe line A and lobe line B both indicate a fold line to be completed after the folding along the folded edge.

FIG. 2C illustrates the next step in the construction of the autologous tissue replacement heart valve. FIG. 2C shows the folded dissected pericardial tissue 44, now with the smooth side 54 facing outward on both sides. Lobe line A and lobe line B indicate a fold location used to form the lobes 46, 48, 50 of the replacement heart valve as illustrated in FIG. 1, along with a first transverse fold line 55 and a second transverse fold line 57, which are illustrated in FIG. 2B. A fold direction 52 is also indicated. This folding step results in a folded angle of approximately 90 to 120 degrees and is not folded flat as in the folding described in regard to FIG. 2B. Once the tissue is folded as illustrated in FIGS. 2B and 2C, the other edges of the new valve, along the commissural and annular margins, would be sewn together in the embodiment shown and described herein. In this configuration, as illustrated in FIG. 1, a first side wall 43 is partially defined by the first transverse fold line 55, the first portion of the first lobe line A, and a first portion of the folded edge line 40. Further, a second side wall 45 is partially defined by the first transverse fold line 55, the second transverse fold line 57, a second portion of the first lobe line A, and a second portion of the folded edge line 40. Also, a third side wall 47 is partially defined by the second transverse fold line 57, a third portion of the first lobe line A, and a third portion of the folded edge line 40. So configured, the first, second, and third portions of the first lobe line define a top perimeter edge 49, 51, 53, respectively, of each of the first side wall 43, the second side wall 45, and the third side wall 47 that cooperates to form a triangular shape when the tissue if folded as illustrated in FIG. 1. Further folds in the tissue along the three commissural edges can provide additional reinforcement to the valve in these high stress areas. By not treating and otherwise compromising the autologous tissue, the potential for valve growth and remodeling is most likely enhanced. Furthermore, since this material is harvested from the same patient, immunologic rejection is not a risk like it is from tissue in cadaver or other species, i.e., a xenograft.

The resulting replacement valve provides a substrate that permits ergonomic handling under typical operating room conditions for autologous, still viable tissue. Better means may be employed to enable reliable trimming and reinforcement of non-preserved pericardium. Customized valve shapes can also enhance the ability to sew this valve into the appropriate location in the patient's heart. By providing a double layer of pericardial tissue, the inner surface can be oriented not only the LV side but also towards the aortic side. The rougher outer surface of the pericardium is folded and sandwiched between the exposed inner surfaces.

The embodiment described herein provides a more durable and more readily handled replacement valve made from non-preserved viable autologous pericardium. The smooth inner surface of the pericardium is exposed to circulating blood while the outer pericardium surface, which can be more course even after debridement, is isolated within the folded pericardial tissue planes. Additional folds can provide reinforcement layers of areas under stress, such as the commissural edge sewing points.

Figure 3:
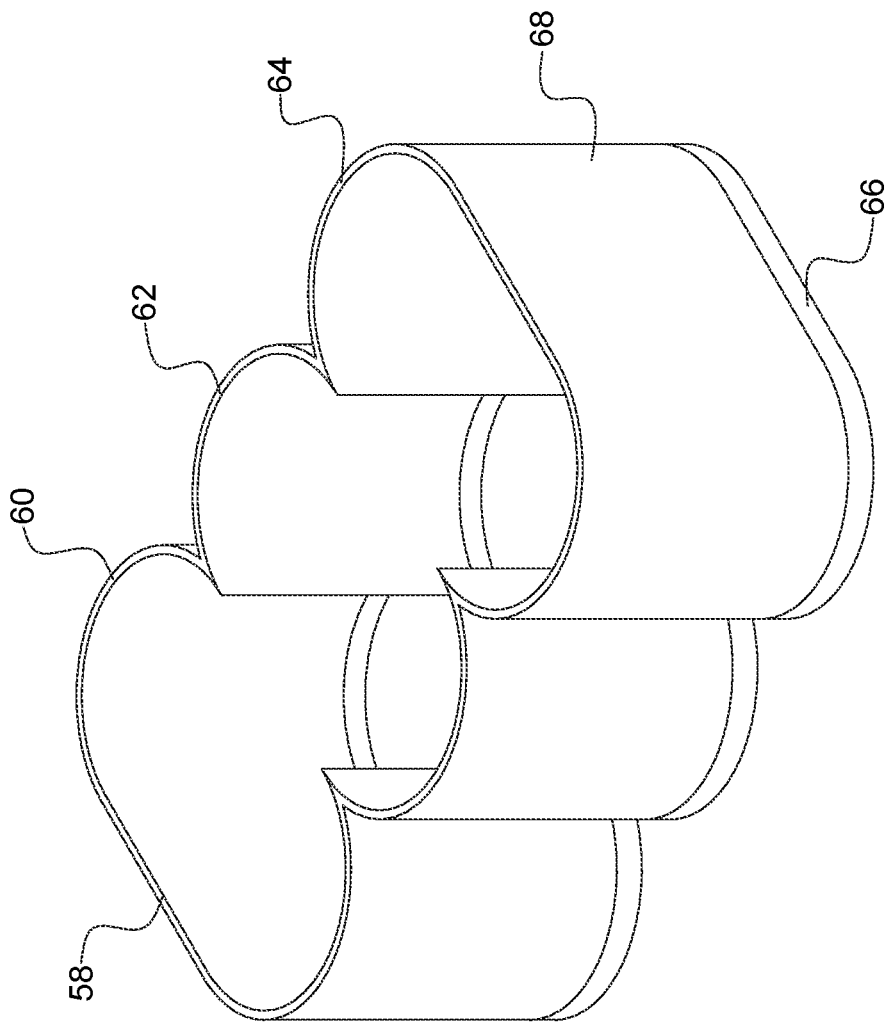
FIG. 3 is a top-left-front perspective view of a template for constructing a repair structure for cardiac surgery.

FIG. 3 is a top-left-front perspective view of a template 56 for constructing a repair structure for cardiac surgery. The template 56 is shown having a frame 58 including several lobe structures 60, 62, 64 and a sidewall 68 traversing the entire template structure. The template 56 also includes a sharpened edge 66, which may be used to cut or dissect pericardial or other suitable tissue. This may eliminate the need to manually trace a template shape or incrementally dissect a suitable autologous tissue for use in the repair structures described herein. The template 56 illustrated in FIG. 3 is not necessarily to scale, and the dimensions of the template may be varied to accommodate variations in anatomical structures unique to each patient.

Alternate embodiments may include other autologous tissue holding or dissecting devices for maintaining stationary tissue with which to work and form a heart valve replacement or other cardiac repair structure. Such a tissue holding device could include the placement of harvested tissue onto a porous platform, for example, foam, or otherwise stabilizing base. The porous material could be impregnated with a glucose solution containing electrolytes in order to maintain tissue health and prevent desiccation. The tissue holding device could be implemented with or without applied suction via a vacuum generator or source or other means, as known in the art. The suction and porous platform stabilization, whether used together or separately, provide a stable base for completing the dissection and formation of tissue into a suitable cardiac repair structure. Additional minimally invasive sewing or suturing devices may also be employed to facilitate suture placement or semi-automated suturing.

Figure 4:
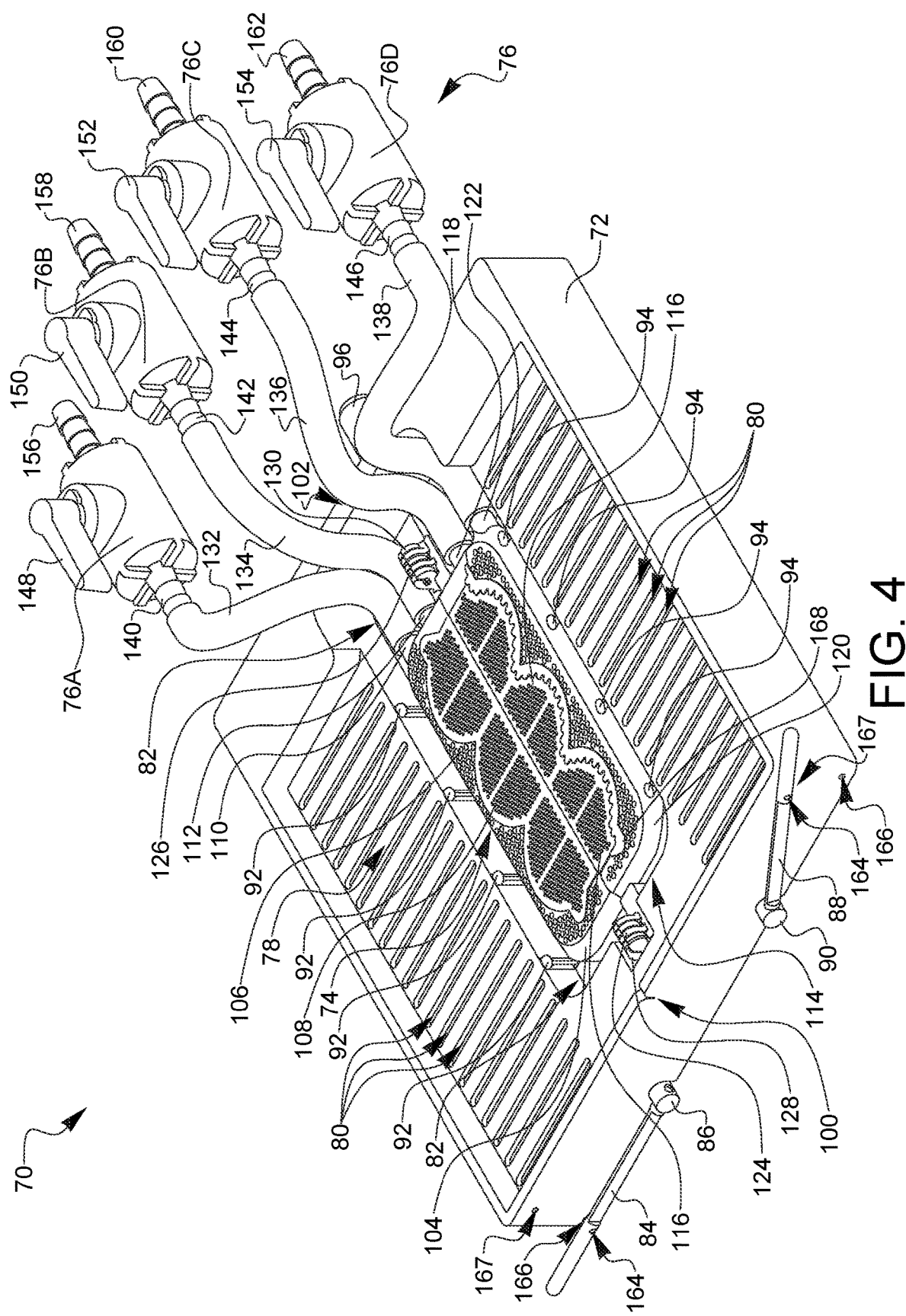
FIG. 4 is a top front right perspective view of a repair structure apparatus for cardiac surgery.

FIG. 4 is a top front right perspective view of a repair structure apparatus for cardiac surgery. A repair structure apparatus 70 is a precision workstation used in constructing a heart valve or other repair structure used in cardiac surgery which is composed of a patient's own harvested pericardial tissue. The repair structure apparatus 70 has a deck 72 used as a base structure and workstation. The deck 72 defines a first fluid reservoir 78 and a second inner fluid reservoir 82 which is lower than and inset within the fluid reservoir 78. The fluid reservoir 78 further defines a plurality of fluid channels 80 on either side of the fluid reservoir 78. The fluid reservoir 78 is in communication with the second inner fluid reservoir 82. The inner fluid reservoir 82 is sized and configured to receive and hold a platform 74 consisting of several interlocking components. The platform 74 has a first platform segment, or half, 104 having a first port 110 and a second port 112 on one end and a first porous surface section 106 on the top surface consisting of a plurality of small apertures in communication with a first internal chamber and the first port 110. The first platform segment 104 also has a second porous surface section 108 consisting of a plurality of small apertures in communication with a second internal chamber and the second port 112. The platform 74 also has a second platform segment, or half, 114 which has a separate third platform section 116 and a separate fourth platform section 120. The third platform section 116 defines a plurality of small apertures in communication with a third internal chamber and a third port 118. The fourth platform section 120 also defines a plurality of small apertures in communication with a fourth internal chamber and a fourth port 122 as well as an alignment edge 168 which is configured to align a cutting template, such as set forth herein, for cutting a portion of harvested pericardial tissue in a specific pattern to subsequently construct a cardiac repair structure, such as a replacement heart valve. The first platform segment 104 and the second platform segment 114 are held together by a first hinge 124 and a second hinge 126. A first hinge pin 128 and a second hinge pin 130 hold the hinges 124, 126 securely together. The first hinge 124 and the second hinge 126 are configured such that the first platform segment 104 of the platform 74 can be rotated approximately 180-degrees to fold onto the second platform segment 114 during the procedure described herein.

The deck 72 also defines a first suture channel 100 and a second suture channel 102 on opposite sides of the deck 72, each configured to releasably hold or temporarily restrict movement of a suture held within one of the channels 100, 102. A first clamp lever 84 having a pin 164 is coupled to a first rotational shaft 86, which is held below the deck 72. Several pins 92 are attached along the length of the first rotational shaft 86, the details and operations of which will be discussed in further detail later. When the first rotational shaft 86 is positioned in an open or unlocked position, as shown here, the pins 92 attached to the first rotational shaft 86 are rotated outward and the pin 164 of the clamp lever 84 is releasably held in a lower pin recess 166 defined by the deck 72. As the first rotational shaft 86 is rotated to a closed or locked position, each of the pins 92 attached along the length of the first rotational shaft 86 are rotated inward to hold the platform 74 in place and the pin 164 is then releasably held in an upper pin recess 167 defined by the deck 72. A second clamp lever 88 having a pin 164 is coupled to a second rotational shaft 90, which is also held below the deck 72. Several pins 94 are attached along the length of the second rotational shaft 90, the details and operations of which will be discussed in further detail later. When the second rotational shaft 90 is positioned in an open or unlocked position, the pins 94 attached to the second rotational shaft 90 are rotated outward and the pin 164 of the clamp lever 88 is releasably held in a lower pin recess 166 defined by the deck 72. As the second rotational shaft 90 is rotated to a closed or locked position, as shown in FIG. 4, each of the pins 94 attached along the length of the second rotational shaft 90 are rotated inward to hold the platform 74 in place and the pin 164 is then releasably held in an upper pin recess 167 defined by the deck 72.

The repair structure apparatus 70 also includes a manifold or vacuum array 76 which includes four separate vacuum channels, a first vacuum channel 76A, a second vacuum channel 76B, a third vacuum channel 76C, and a fourth vacuum channel 76D. A first tube 132 connected to the first port 110 of the platform 74 on one end and to a first entrance fitting 140 on another end provides continuity between the first chamber in the first platform segment 104 and the first vacuum channel 76A. First vacuum channel 76A also has a first stopcock 148 for turning on and off the flow of vacuum and a first source fitting 156 leading to a vacuum source. A second tube 134 connected to the second port 112 of the platform 74 on one end and to a second entrance fitting 142 on another end provides continuity between the second chamber in the first platform segment 104 and the second vacuum channel 76B. Second vacuum channel 76B also has a second stopcock 150 and a second source fitting 158 leading to a vacuum source. A third tube 136 connected to the third port 118 of the platform 74 on one end and to a third entrance fitting 144 on another end provides continuity between the third chamber in the first platform segment 104 and the third vacuum channel 76C. Third vacuum channel 76C also has a third stopcock 152 and a third source fitting 160 leading to a vacuum source. A fourth tube 138 connected to the fourth port 122 of the platform 74 on one end and to a fourth entrance fitting 146 on another end provides continuity between the fourth chamber in the first platform segment 104 and the fourth vacuum channel 76D. Fourth vacuum channel 76D also has a fourth stopcock 154 and fourth source fitting 162 leading to a vacuum source. The arrangement and configuration of the platform 74 in this embodiment may be alternatively arranged in other embodiments. For example, while four sections of the platform 74 are shown herein, other embodiments may have fewer or possibly more sections in the platform. Alternate embodiments may include a deck with other shapes or configurations such as oval, circular, or otherwise arranged, as well as alternate fluid reservoir arrangements, such as more than two fluid reservoirs as required by specific surgical protocols or other parameters of operative strategy. While four independent vacuum channels are shown here, they are shown in that manner for demonstrative purposes only. Other embodiments may have fewer or greater numbers of vacuum channels or be arranged in other manners than shown herein.

Figure 5A:
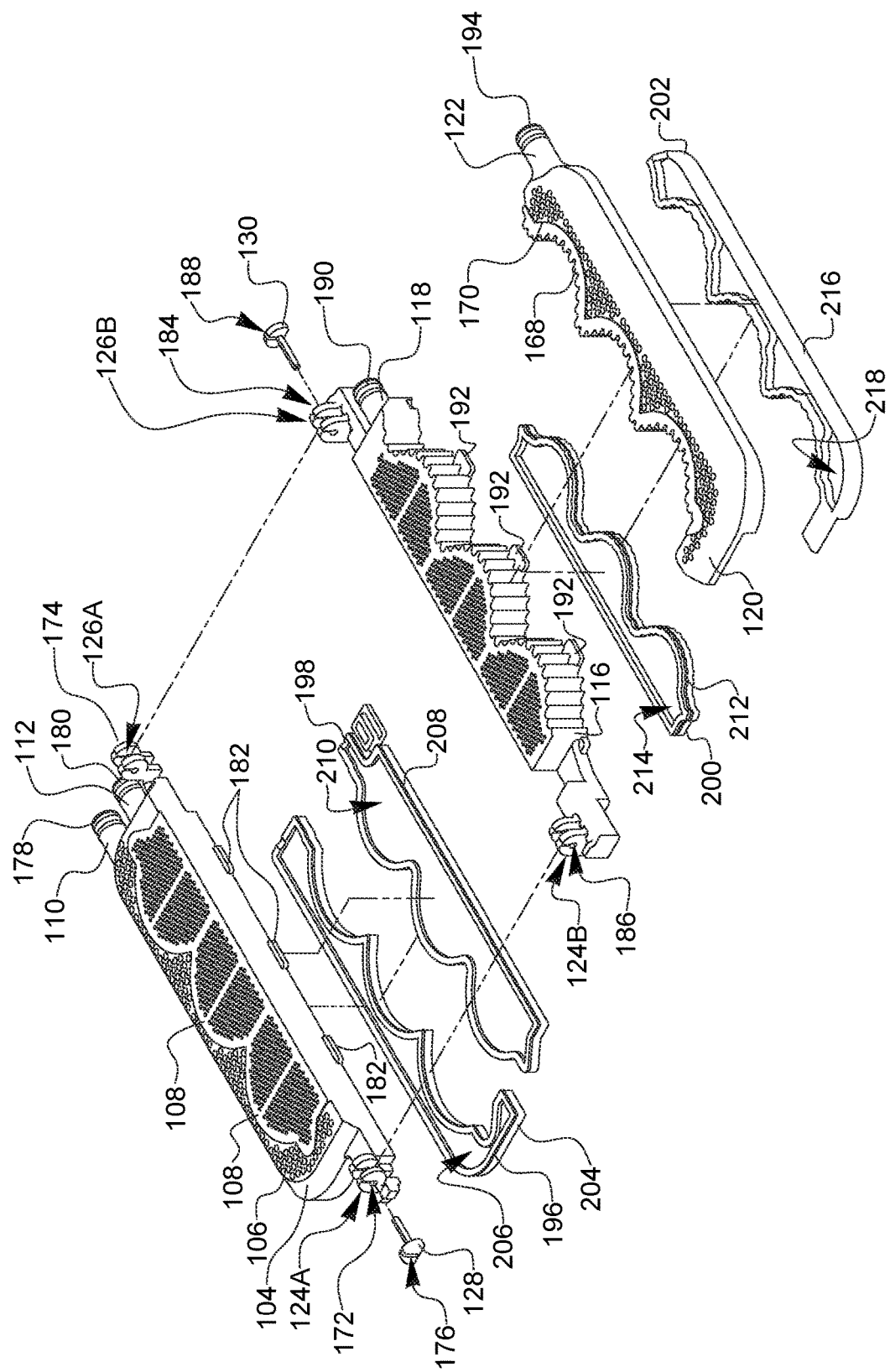
FIGS. 5A-5C are exploded views illustrating the assembly of the repair structure apparatus for cardiac surgery of FIG. 4.
Figure 5B:
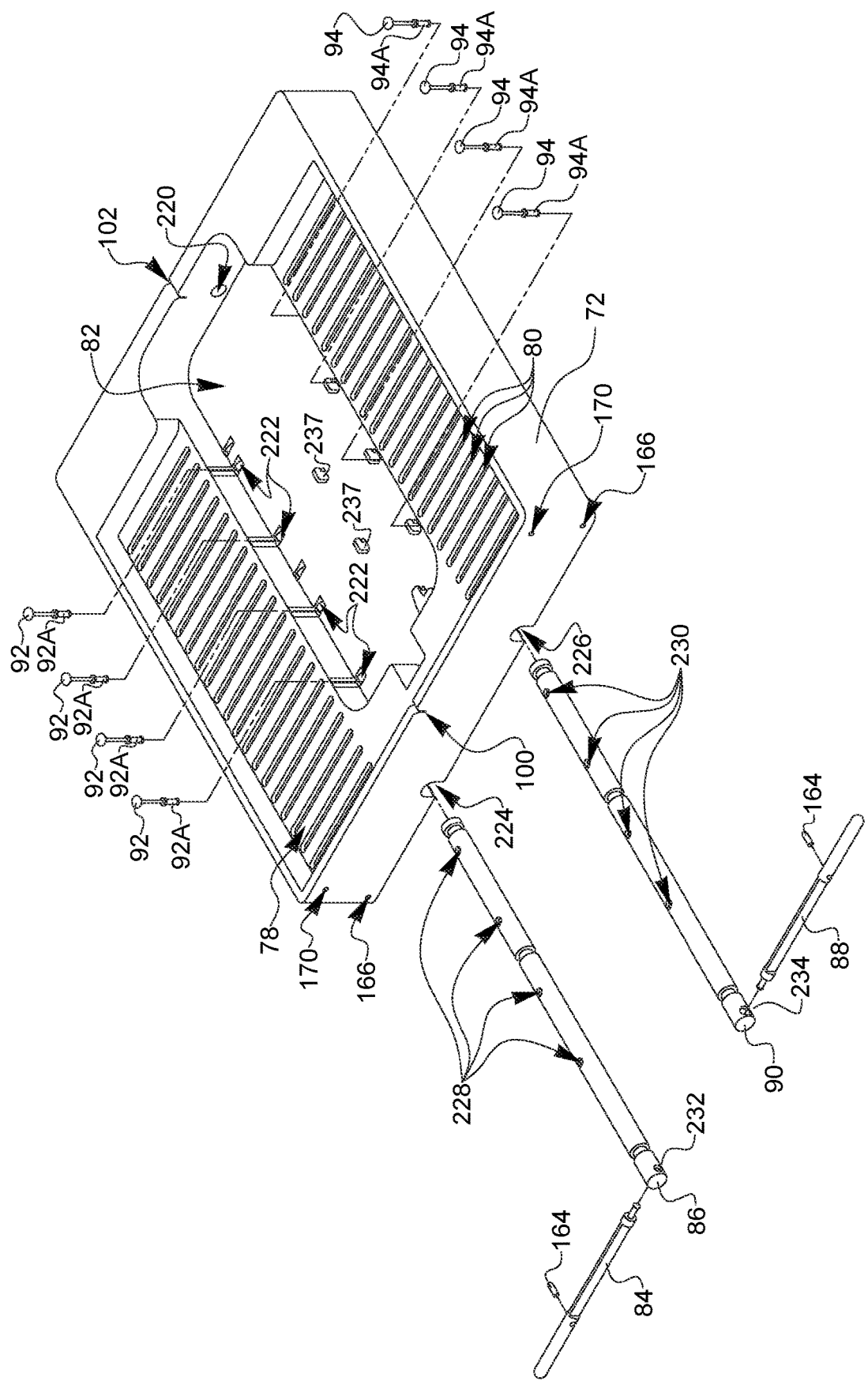
Figure 5C:
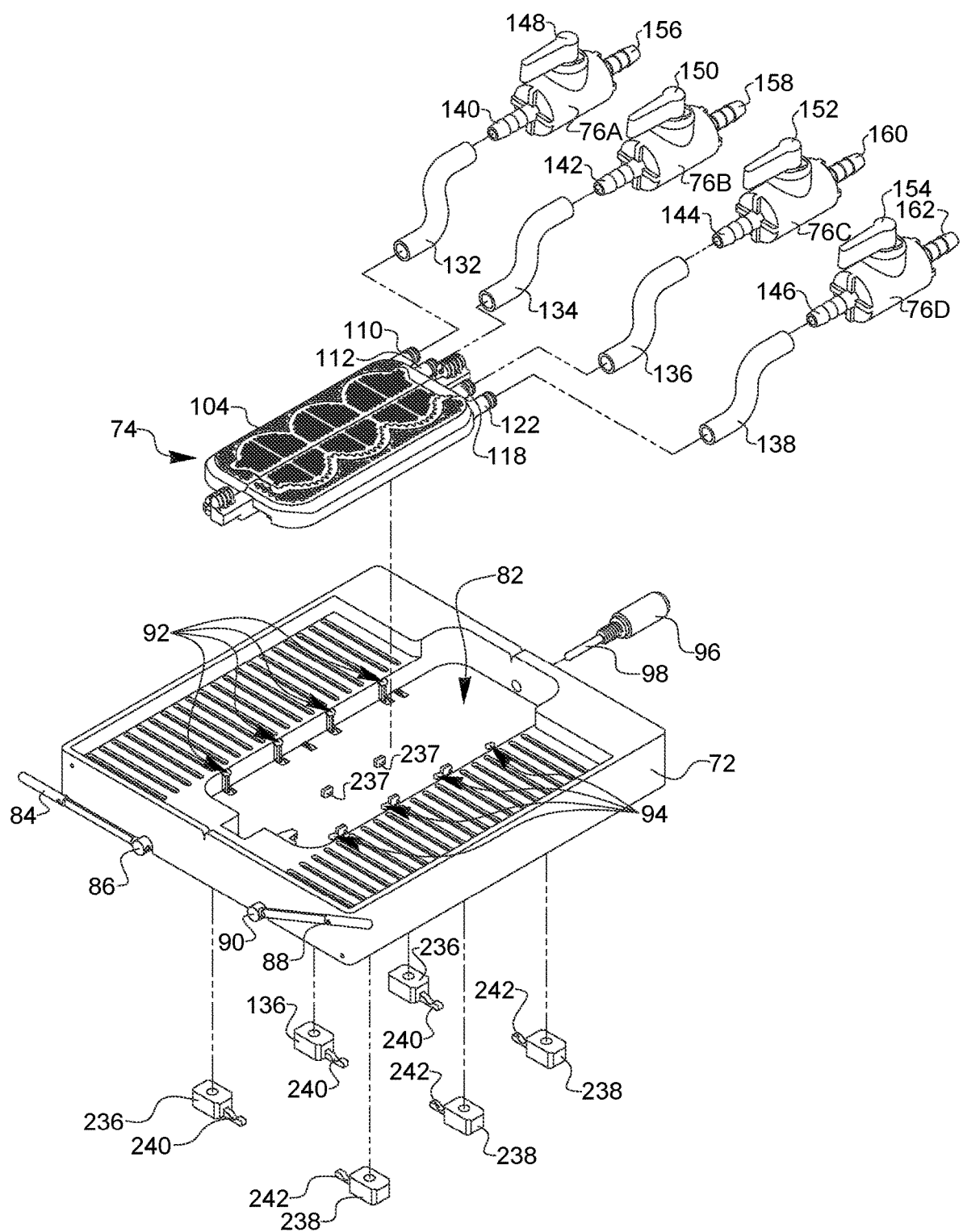

FIGS. 5A-5C are exploded views illustrating the assembly of the repair structure apparatus for cardiac surgery of FIG. 4. FIG. 5A illustrates several assembly steps related to the platform 74. The first platform segment 104 having a first porous surface section 106, second porous surface section 108, first port 110, and second port 112 also defines several alignment tabs 182 configured to align and mate with other portions of the platform 74 and a first hinge portion 124A and a second hinge portion 126A at either end. The first port 110 has a barbed end 178 and the second port 112 has a barbed end 180. The first hinge portion 124A further defines a pin path 172 and the second hinge portion 126A further defines a pin path 174. A first lower chamber floor 196 which defines a sealing edge 204 that outlines and establishes a first chamber 206 is attached and mated to the bottom of the first platform segment 104, corresponding to the first porous surface section 106 of the first platform segment 104. This establishes the first chamber 206 within the platform 74 that is in communication with both the first porous surface section 106 and the first port 110. A second lower chamber floor 198 which defines a sealing edge 208, and a second chamber 210, is mated to the bottom of the first platform segment 104, corresponding to the second porous surface section 108 within the first platform segment 104. This establishes the second chamber 210 within the platform 74 that is in communication with both the second porous surface section 108 of the first platform segment 104 and the second port 112.

The third platform section 116, having a porous surface defined by a plurality of holes, also defines several alignment tabs 192 configured to mate and align with other corresponding features of the deck 72. The third platform section 116 also defines a third port 118 having a barbed end 190, a first hinge portion 124B and a second hinge portion 126B at either end. The first hinge portion 124B further defines a pin path 186 and the second hinge portion 126B further defines a pin path 184. A third lower chamber floor 200 which defines a sealing edge 212, and a third chamber 214 is mated to the bottom of the third platform section 116, corresponding to the porous surface defined by the third platform section 116. This establishes the third chamber 214 within the platform 74 that is in communication with both the porous surface defined by the third platform section 116 and the third port 118. The fourth platform section 120, having a porous surface defined by a plurality of holes, also defines an alignment edge 168 with an outer lip 170 and a fourth port 122 having a barbed end 194. A fourth lower chamber floor 202 which defines a sealing edge 216 and a fourth chamber 218 is mated to the bottom of the fourth platform segment 120, corresponding to the porous surface defined by the fourth platform section 120. This establishes the fourth chamber 218 within the platform 74 that is in communication with both the porous surface defined by the fourth platform section 120 and the fourth port 122. The fourth platform section 120 is coupled to the third platform section 116 by mating the third platform section 116 with the fourth platform section 120. Next, the second platform section of the first platform segment 104 is coupled to the third platform section 116 by intermeshing both the first hinge portions 124A, 124B to create first hinge 124 and the second hinge portions 126A, 126B. At or near the same time the alignment tabs 182 on first platform segment 104 line up with a corresponding receiving feature on the third platform section 116. To secure the hinges 124, 126 together, a first hinge pin 128 defining a suture channel 176 and second hinge pin 130 defining a suture channel 188 are inserted into first hinge 124 and second hinge 126 to lock the first hinge portions 124A, 124B and second hinge portions 126A, 126B in place, respectively. Porous surfaces may be created by a plurality of holes in the surface or be fabricated from a section or piece of fritted glass or ceramic, or other surface material providing a porous surface configured to be in fluid communication with a chamber within one or more segments of alternate embodiments of platforms. Some surfaces may have a plurality of holes, while others may be fashioned of fritted glass or other materials.

FIG. 5B illustrates a next step in the assembly of the repair structure apparatus for cardiac surgery of FIG. 4. FIG. 5B illustrates several assembly steps related to the deck 72. Within the inner fluid reservoir 82 are several slots 222 related to the first rotational shaft 86, two retaining tabs 237 for securing the platform 74, and a hole 220 configured to receive the knob 96 and knob shaft 98. While not visible, there are additional slots on the opposite side related to the second rotational shaft 90. The deck also defines a hole 224 for receiving the first rotational shaft 86 and a second hole 226 for receiving the second rotational shaft 90. Pin 164 is inserted into the clamp lever 84 and the clamp lever 84 is inserted into a hole 232 on the first rotational shaft 86. The first rotational shaft 86 also has several holes 228 along its length that spatially correspond to the locations of the slots 222 in the inner fluid reservoir 82 of the deck 72. Once the first rotational shaft 86 is inserted into hole 224, each pin 92 having a pin insert 92A is inserted through each slot 222 and into a corresponding hole 228 on the first rotational shaft 86. Thus, when the first rotational shaft 86 is rotated, the pins 92 rotate along with the first rotational shaft 86. A second pin 164 is inserted into the clamp lever 88 and the clamp lever 88 is inserted into a hole 234 on the second rotational shaft 90. The second rotational shaft 90 also has several holes 230 along its length that spatially correspond to the locations of the slots, not visible here, in the inner fluid reservoir 82 of the deck 72. Once the second rotational shaft 90 is inserted into hole 226, each pin 94 having a pin insert 94A is inserted through each slot and into a corresponding hole 230 on the second rotational shaft 90. Thus, when the second rotational shaft 90 is rotated, the pins 94 rotate along with the second rotational shaft 90.

FIG. 5C illustrates a next step in the assembly of the repair structure apparatus for cardiac surgery of FIG. 4. FIG. 5C illustrates several assembly steps related to the completion of the deck assembly, attachment of the platform 74 and assembling the vacuum array 76. Several first shaft retainers 236 each having an arm 240 are secured into the bottom of the deck 72 to fixedly attach the first rotational shaft 86 in place. Several more second shaft retainers 238 each having an arm 242 are secured into the bottom of the deck 72 to fixedly attach the second rotational shaft 90 in place. Each vacuum tube 132, 134, 136, 138 is attached on one end to the platform 74 at first port 110, second port 112, third port 118, and fourth port 122, respectively. The opposite ends of each vacuum tube 132, 134, 136, 138 are attached to the first entrance fitting 140 on the first vacuum channel 76A, second entrance fitting 142 on the second vacuum channel 76B, third entrance fitting 144 on the third vacuum channel 76C, and fourth entrance fitting 146 on the fourth vacuum channel 76D, respectively. The platform 74 is then placed inside the second inner fluid reservoir 82 of the deck 72 and partially secured by sliding and locking onto the retaining tabs 237 in the bottom of the second inner fluid reservoir 82. Corresponding features, not shown here, are located on the underside of the platform 74. The first clamp lever 84 and the first rotational shaft 86 as well as the second clamp lever 88 and second rotational shaft 90 are also rotated inwards, such that the pins 92 attached to the first rotational shaft 86 and the pin 94 attached to the second rotational shaft 90 also engage to hold the platform 74 in place from the sides. Finally, the knob shaft 98 of the knob 96 is inserted into the side of the platform 74, which is not visible here, to be able to actuate for the purpose of rotating the first platform segment 104 of the platform 74.

Figure 6A:
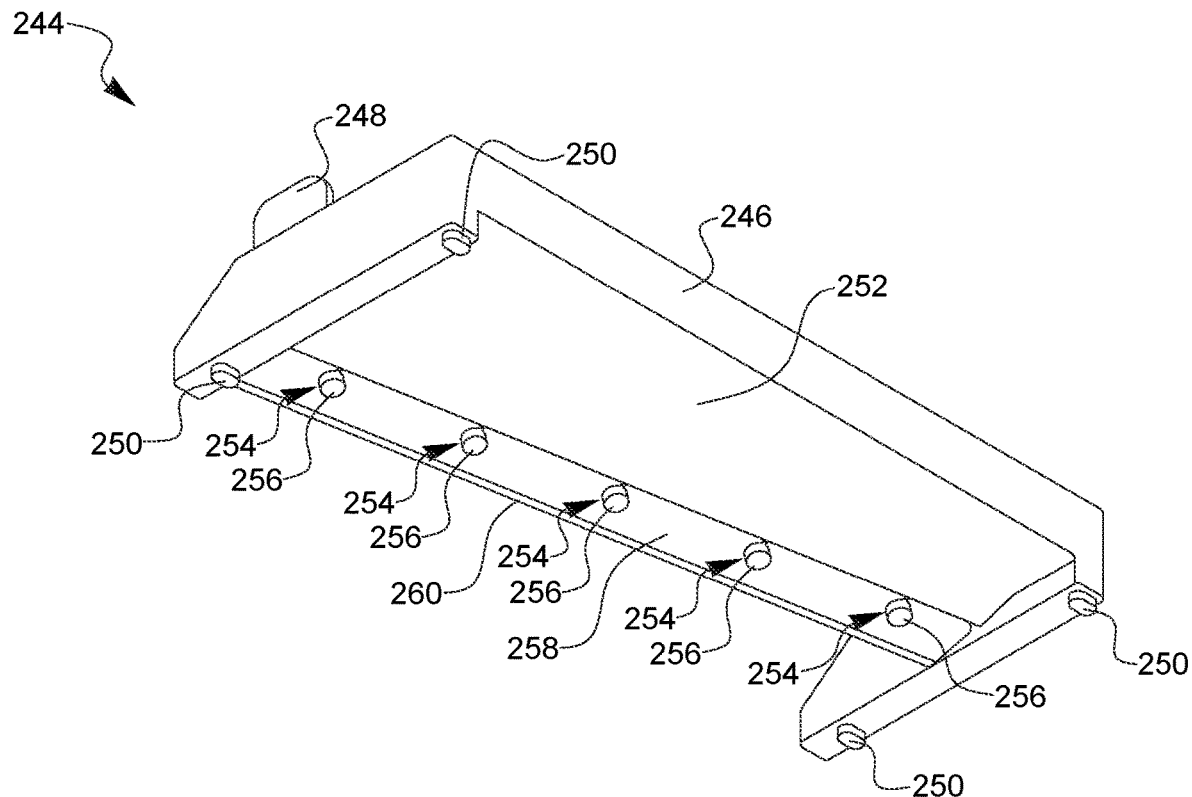
FIGS. 6A-6H are illustrative views of additional surgical implements used in conjunction with the repair structure apparatus for cardiac surgery of FIG. 4.
Figure 6B:
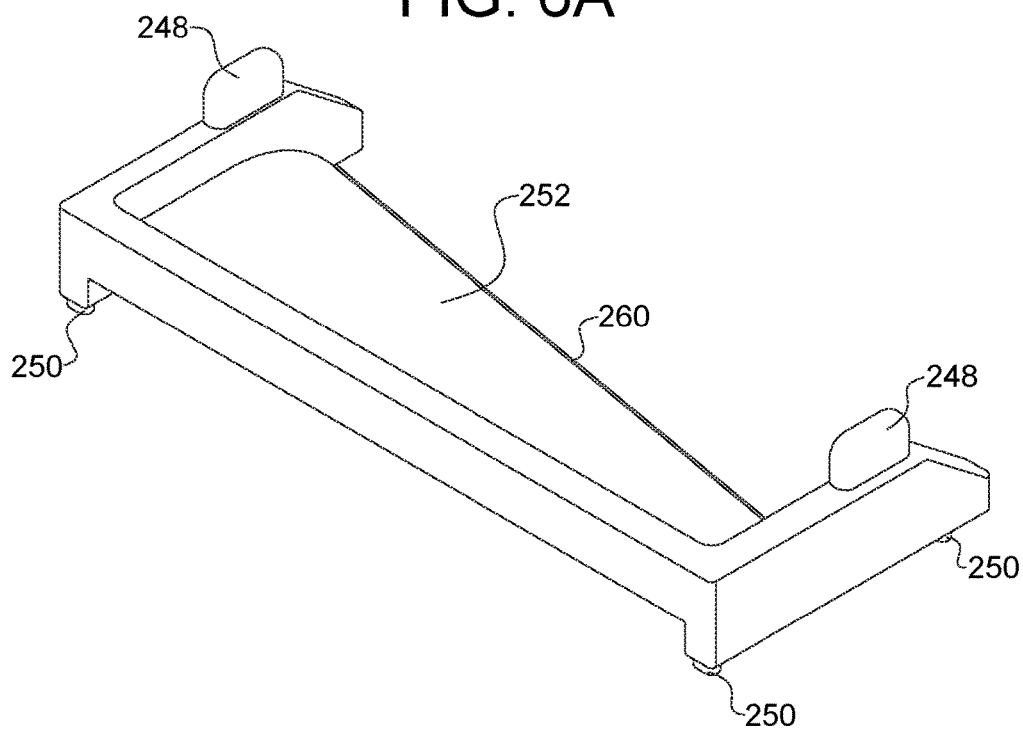

FIGS. 6A-6H are illustrative views of additional surgical implements used in conjunction with the repair structure apparatus for cardiac surgery of FIG. 4. FIG. 6A is a bottom-left-rear perspective view of a slicing sled 244 for use in conjunction with the repair structure apparatus of FIG. 4. The slicing sled 244 is a device utilized for thinly slicing rough tissue from a top surface of a section of pericardial or other tissue used in cardiac repair structures. The slicing sled 244 has a frame 246 with a handle 248 on either side, and several offsets 250 placed on the bottom of the frame 246. Each offset 250 is configured to provide a space between the bottom of the frame 246 and a blade 258 attached to a blade support 252 which spans the frame 246 of the slicing sled 244. The blade support 252 also defines several blade retainers 256 along the length of the blade support 252. The surgical grade stainless steel blade 258 defines a blade edge 260 and several blade recesses 254 along the length of the blade 258 that receive the blade retainers 256 and fixedly attach the blade 258 to the bottom of the slicing sled 244. FIG. 6B is a top-right-rear perspective view of the slicing sled 244 for use in conjunction with the repair structure apparatus of FIG. 4. While the blade 258 is fabricated from a surgical grade stainless steel, other materials suitable for surgical procedures may alternatively used as appropriate. Other configurations or embodiments having a set or adjustable thickness of cutting height may also be used in alternate embodiments.

Figure 6C:
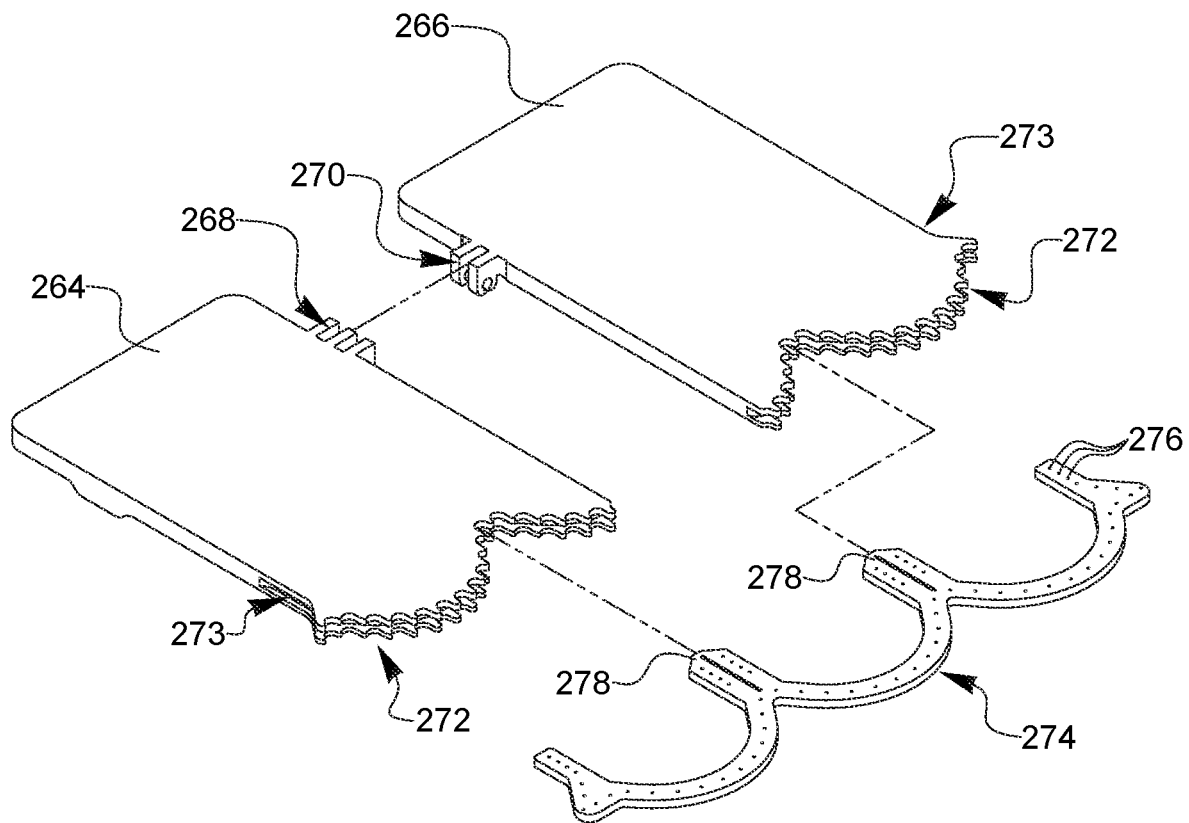
Figure 6D:
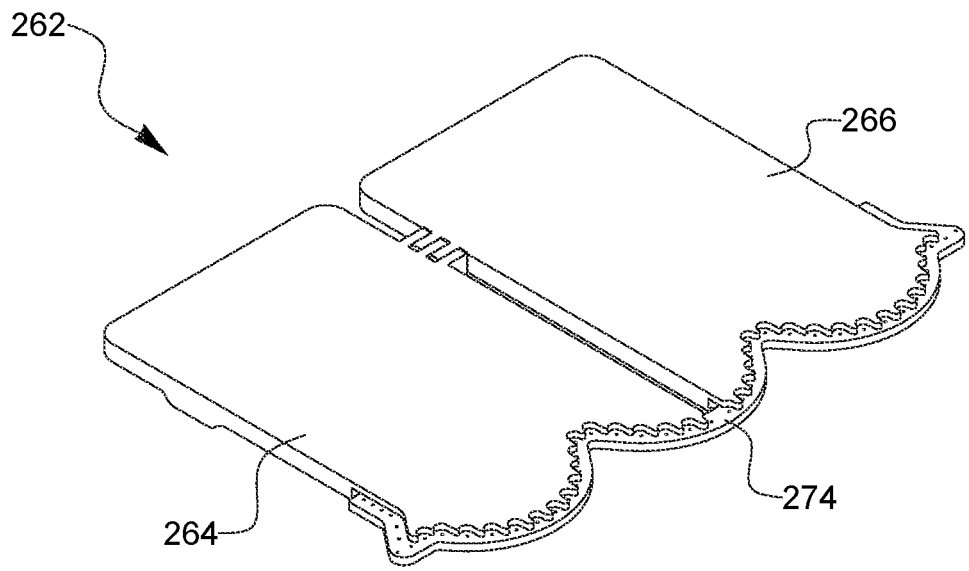

FIG. 6C is an exploded view of the assembly of a folding felt holder 262 used in conjunction with the repair structure apparatus for cardiac surgery of FIG. 4, a perspective view of which is shown in FIG. 6D. A first folding member 264 defining a slot 273 and hinge 268 is interlocked and combined with a second folding member 266 which defines a slot 273 and a hinge 270. The hinge 268 and hinge 270 combine to form a folding hinge between the first folding member 264 and the second folding member 266 of the folding felt holder 262. Each of the first folding member 264 and the second folding member 266 each have scallops 272 on one end that correspond to potential stitching sites for the cardiac repair structure. A felt support 274 having a plurality of guide apertures 276 and two slots 278 is then inserted into the slot 273 in each portion 264, 266 of the folding felt holder 262.

Figure 6E:
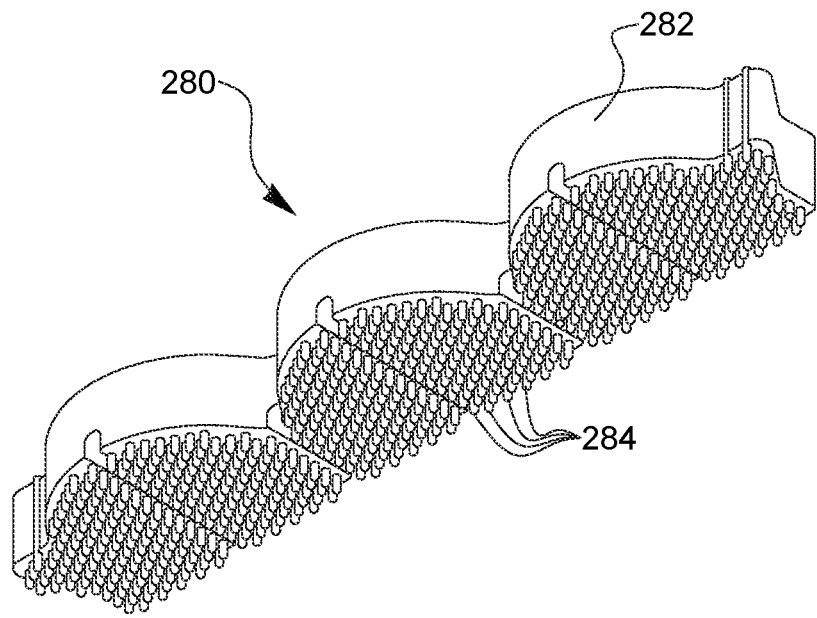
Figure 6F:
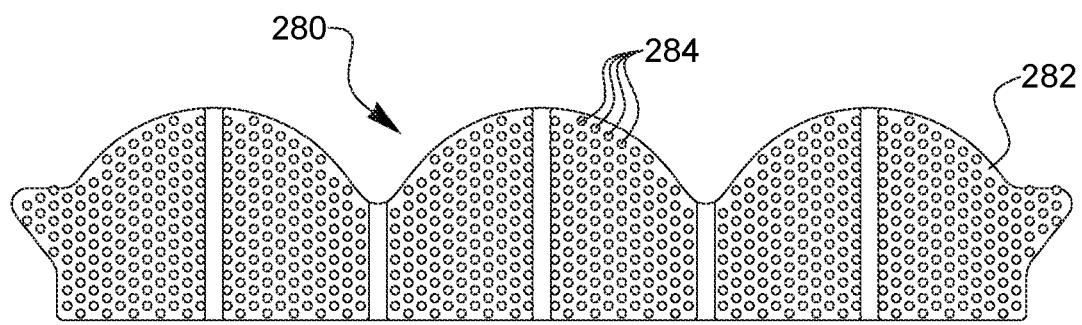

FIG. 6E is a bottom-left-front perspective view of a pin cushion tool 280 used in conjunction with the repair structure apparatus for cardiac surgery of FIG. 4. The pin cushion tool 280 defines a base 282 that corresponds to a shape of both a portion of the first platform segment 104 of the platform 74 as well as an intended shape of the pericardial or other tissue section used in a cardiac repair structure. On the bottom of the pin cushion tool 280 a plurality of pins 284 are further defined. FIG. 6F is a bottom view of the pin cushion tool 280 of FIG. 6E. The pin cushion tool 280 is used to assist in the release of a prepared pericardial tissue used as a cardiac repair structure, the additional details of which will be described later. While a mechanical pin cushion tool is illustrated herein, other methods or apparatus may be used in alternate embodiments to assist in the release of pericardial tissue from the platform, such as compressed air delivery systems, fluid release systems, or others one skilled in the art may employ.

Figure 6G:
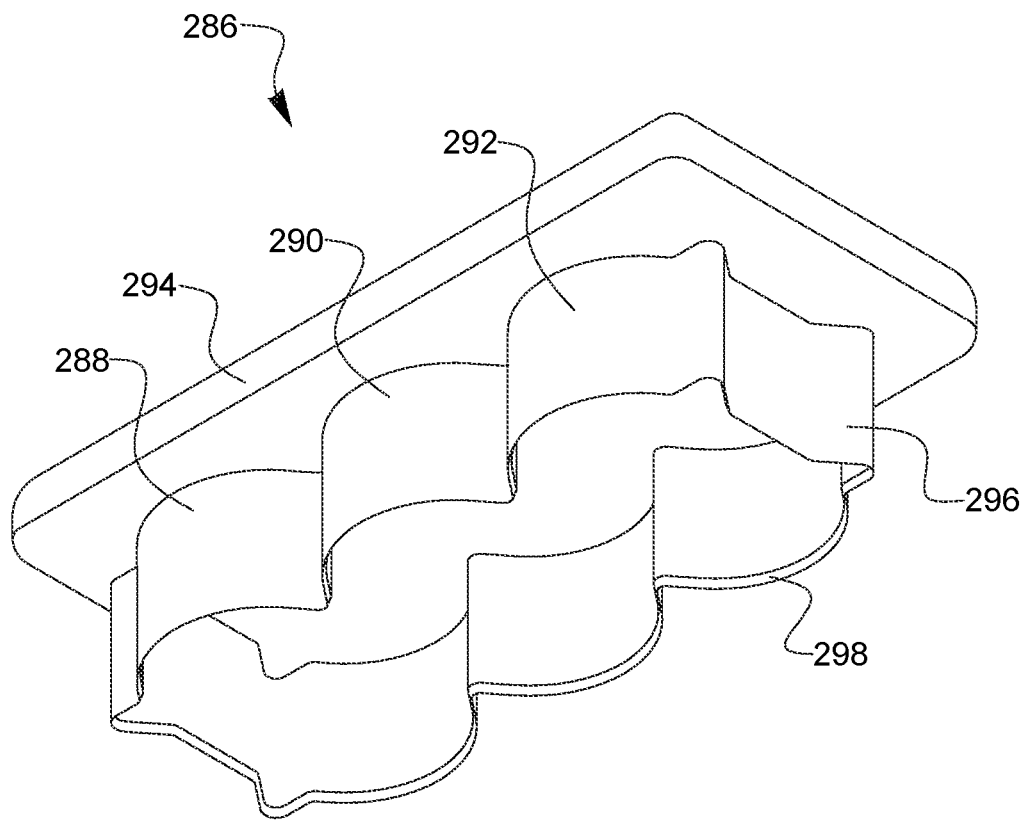
Figure 6H:
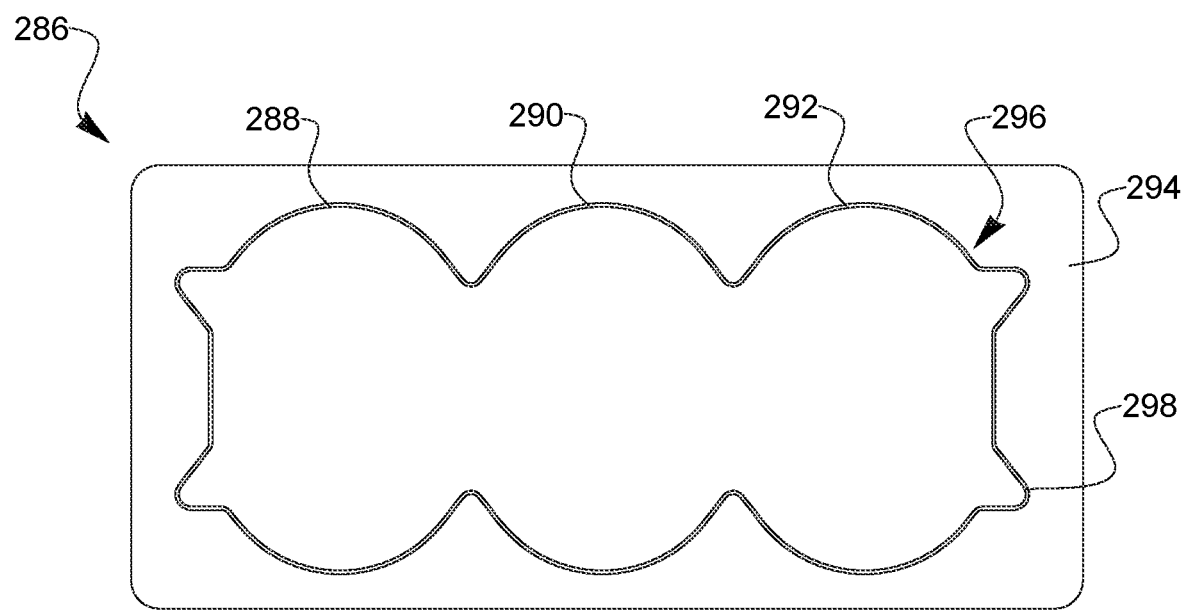

FIG. 6G is a bottom-left-rear perspective view of a cutting template used in conjunction with the repair structure apparatus for cardiac surgery of FIG. 4. A cutting template 286 which defines a base 294 has a frame 296 coupled to the base 294. The base 294 is a rigid material having a cutting edge 298 and is configured and shaped to section a portion if pericardial or other suitable tissue in the shape of a potential cardiac repair structure. The frame has several lobes 288, 290, 292 formed by the frame 296. The additional details describing the use of the cutting template 286 will be described later. FIG. 6H is a bottom view of the cutting template of FIG. 6G.

FIGS. 7A-7H, FIGS. 7J-7N, and FIG. 7P-7Q illustrate a method of use for the repair structure apparatus of FIG. 4 and the additional surgical instruments illustrated in FIGS. 6A-6H. It should be noted that FIGS. 7I and 7O have been omitted so as not to be confused with the numerals 71 and 70, respectively. The utilization of the repair structure apparatus as described herein requires a suitable harvested pericardial tissue, preferably from the patient's own autologous pericardial tissue. It should be noted that while a set of particular surgical procedural steps is described, preferential surgical techniques or medical necessity may result in alternate procedural steps or techniques other than those described being employed. A typical procedure for pericardial tissue harvesting would begin with subxiphoid access for pericardial sac harvest. Access to the anterior middle medial spinal space is achieved via a subxiphoid skin incision along with a dissection under the xiphoid process. A retractor is then used to elevate the sternum away from the heart and the pericardium is carefully evaluated to identify the full length of both the right and left phrenic nerves running along the pericardium. Hemostatic harvest of the pericardial tissue is performed from just the anterior to the phrenic nerves on both sides with special care taken to preserve the bloody supply to the pericardium tissue for as long as possible during the operation. Once harvested, the pericardium is split into a cooled, oxygenated solution having appropriate metabolite and energy characteristics. Appropriate specimen handling and care should be exercised throughout the entire procedure. Tissue preservation can be carried out within standard operating room apparatus or within the second inner fluid reservoir 82 and first fluid reservoir 78 of the deck 72 portion of the repair structure apparatus 70. Accessing the aorta is achieved by making a 5 cm skin incision above the second and third intercostal space on the right anterior chest wall, starting approximately 5 cm from the right sternal border. Cautery is used to transect the intercostal muscles with care being taken to avoid burning too close to the bone, especially on the inferior surface of the second rib to avoid any damage to intercostal nerves or blood vessels. Pleural space is entered in the routine fashion and the right lung is deflated and any adhesions that need to by lysed are addressed. A right superior pulmonary vein shunt is not needed. Next, the ascending aorta proximal to the innominate artery is identified and freed up from attachments to the pulmonary artery, if that is the surgeon's preferred practice. A 16-gauge stainless steel needle with a ball 0.5 cm from its sharp edge is inserted into the aortotomy incision site. Using a separate poke hole, a clamp is placed just proximal to the innominate artery. Antegrade crystalloid cardioplegia is installed to after use of a bolus of adenosine, if that is the surgeon's practice. Upon arrest of the heart, the surgeon's preferred aortotomy incision is made to incorporate the antegrade cardioplegia puncture site. The valve leaflets are resected, decalcification is achieved, and stay sutures are placed at each of the three top commissure sites. Appropriate retraction of the aortic root is achieved and pledgeted 2-0 polyester sutures are equally spaced through the annulus.

Figure 7A:
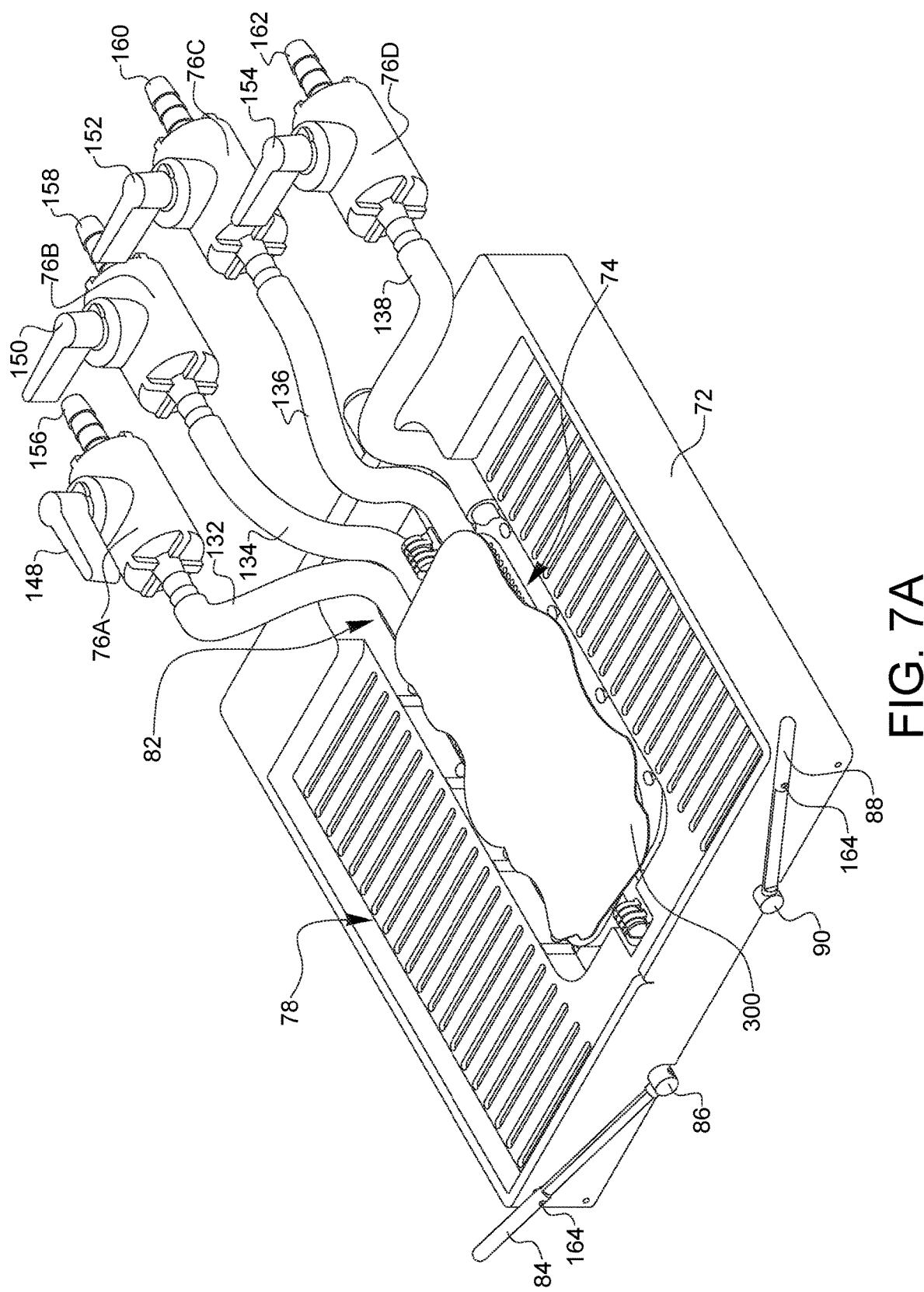

FIG. 7A is a perspective view of the repair structure apparatus for cardiac surgery of FIG. 4. Pericardial tissue preparation requires the use of a precision workstation such as the repair structure apparatus 70 illustrated in FIG. 7A, which includes the rigid docking base or deck 72 with the appropriate accurate alignment features and precise reference surfaces. This repair structure apparatus 70 is used as the central base of this construction process. This docking station has specific reference sites and well controlled surfaces, located in the platform 74, which will be described in further detail herein. Four independently controlled vacuum blocks, also referred to as vacuum chambers, connected to four vacuum channels 76A, 76B, 76C, 76D are used. The blocks articulate together along the axis of the subsequent free edge of the proposed valve. The upper vacuum blocks located within the first platform segment 104 rotate 180-degrees relative to the lower vacuum block within the second platform segment 114 comprised of the separate third platform section 116 and the separate fourth platform section 120. With the diaphragmatic edge oriented towards the top, the parietal layer of the serous pericardium of the pericardial tissue 300 is placed over the vacuum surfaces of both the first platform segment 104 and the second platform segment 114 with the fibrous pericardium facing upward. Appropriate temperature is maintained, and oxygenated physiologic solution is placed on the pericardial specimen within the first fluid reservoir 78 and the second inner fluid reservoir 82. Given the overall arrangement of the second inner fluid reservoir 82 as a lower reservoir within the overall first fluid reservoir 78 the preservative physiologic solution should be introduced into the deck 72 and first fluid reservoir 78 and second inner fluid reservoir 82 such that the pericardial tissue 300 is submersed throughout the procedure. Any large or fatty chunks or segments are cut off or otherwise removed from the exposed fibrous pericardium with care being taken to not perforate the pericardial tissue 300 through and through to smooth down the rough fibrous surface of the pericardium. Any debris is flushed away and removed. As the pericardial tissue 300 is placed onto the platform 74, it should be noted that the position of both the first clamp lever 84 and the second rotational shaft 90 are placed such that the associated pins 92, 94 are holding the platform 74 in place in its flat, stationary configuration. The platform 74 is connected to each of the first vacuum channel 76A, second vacuum channel 76B, third vacuum channel 76C, and fourth vacuum channel 76D by each of the first vacuum tube 132, second vacuum tube 134, third vacuum tube 136, and fourth vacuum tube 138, respectively. While the first source fitting 156, second source fitting 158, third source fitting 160, and fourth source fitting 162 are not shown connected to any vacuum source for the purpose of clarity, it should be known to those skilled in the art the appropriate design and configuration of suitable vacuum sources for such a vacuum array 76 as described herein.

Figure 7B:
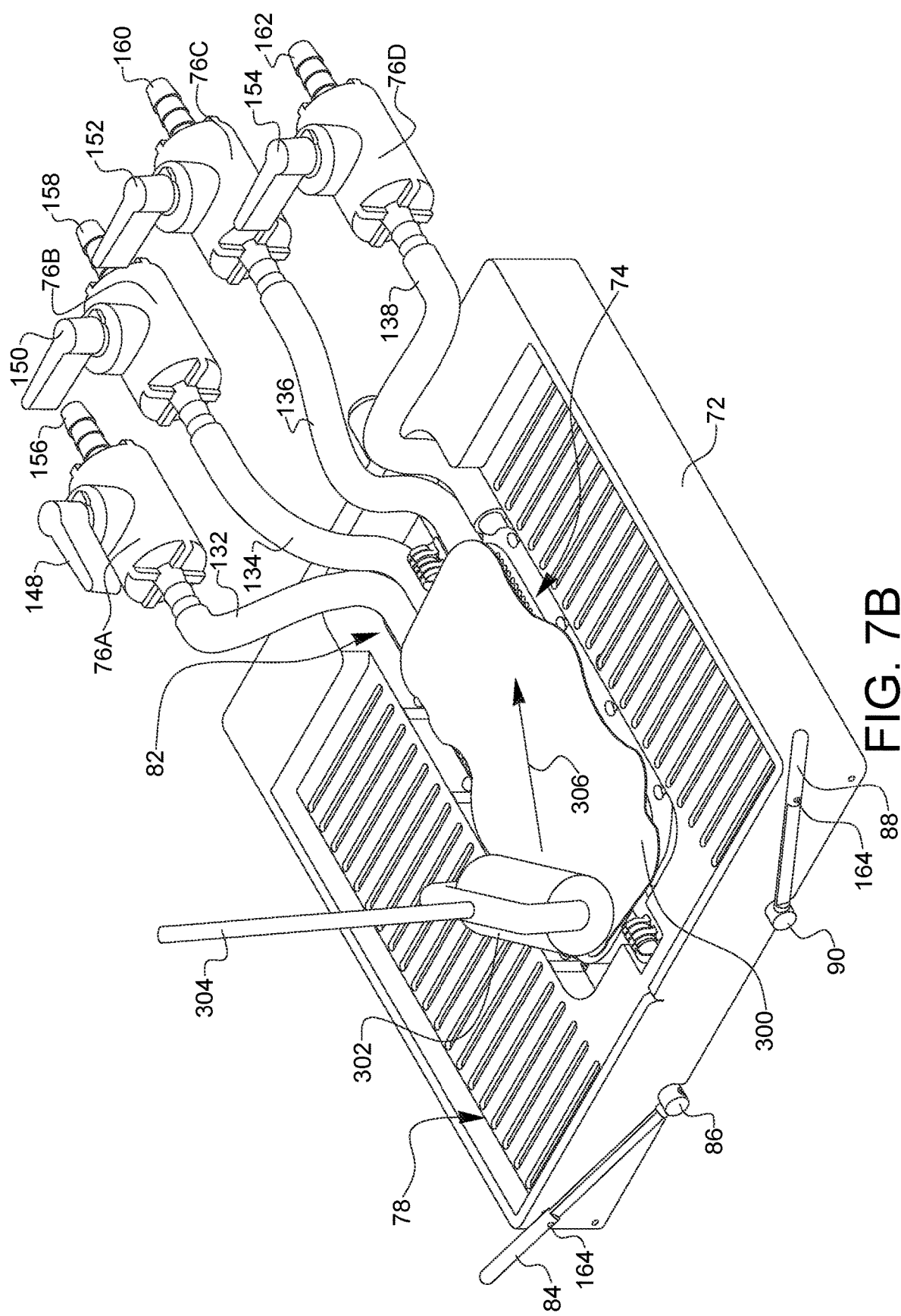
Figure 7C:
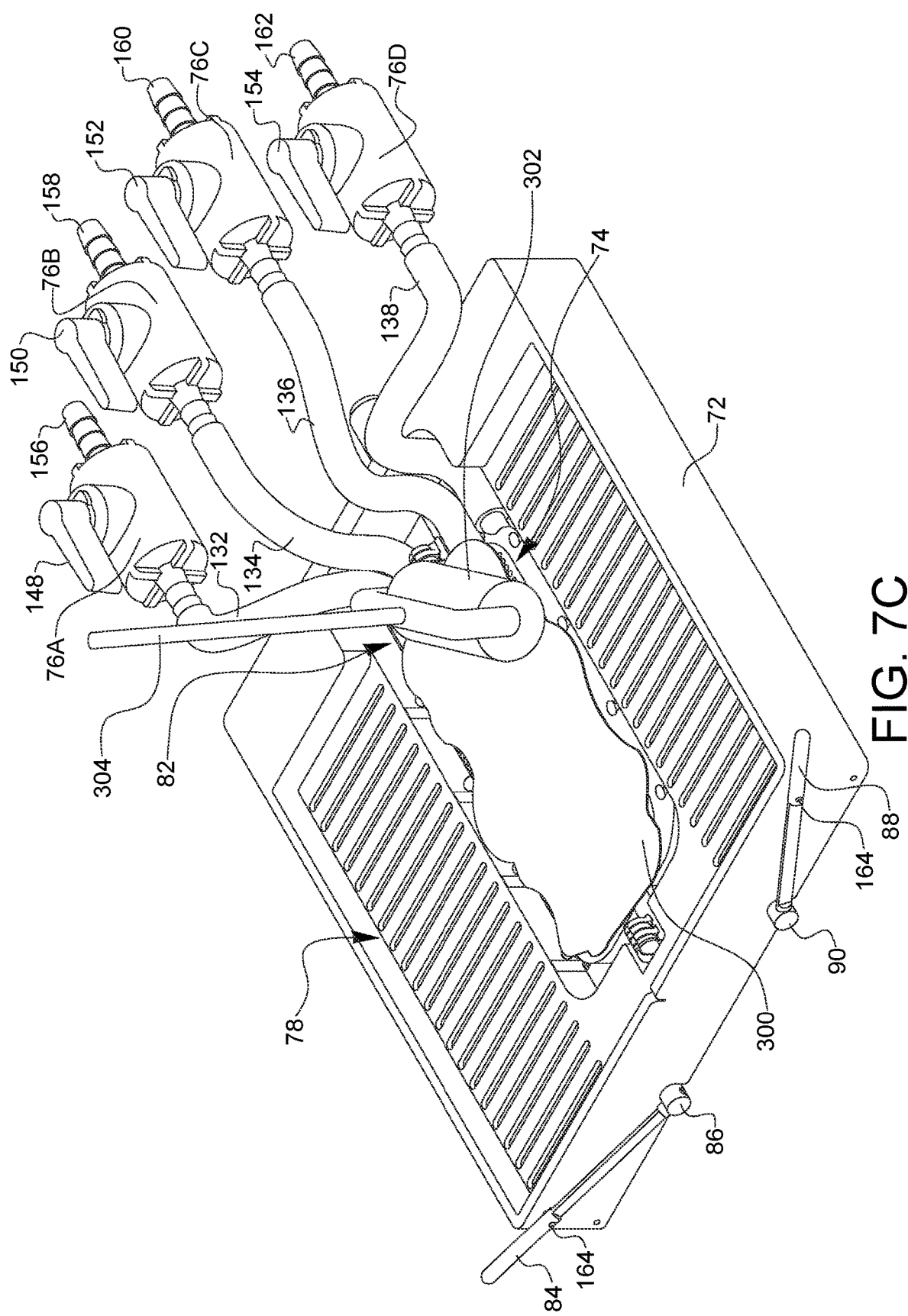

FIG. 7B illustrates subsequent procedural step in using the repair structure apparatus 70. The first vacuum channel 76A is turned on by rotation of the first stopcock 148 to provide a vacuum from below the first vacuum chamber within the first platform segment 104 of the platform 74 on the back platform-facing side of the pericardial tissue 300. The pericardial tissue 300 is smoothed out and stretched across the platform 74. A roller 302 having a handle 304 attached is pressed upon the pericardial tissue 300 and moved in a generally diagonal direction 306 across the pericardial tissue 300 as shown in FIG. 7C. second stopcock 150 of second vacuum channel 76B, third stopcock 152 of third vacuum channel 76C, and fourth stopcock 154 of fourth vacuum channel 76D are turned on to provide a vacuum via all four vacuum chambers within the platform as the roller 302 is used to continuously smooth out and flatten the pericardial tissue 300 against the platform 74. While the stopcock mechanisms for the vacuum channels are shown as quarter turn valves, other means of controlling or regulating the vacuum flow known to one skilled in the art between the vacuum source and the platform may be utilized in alternate embodiments.

Figure 7D:
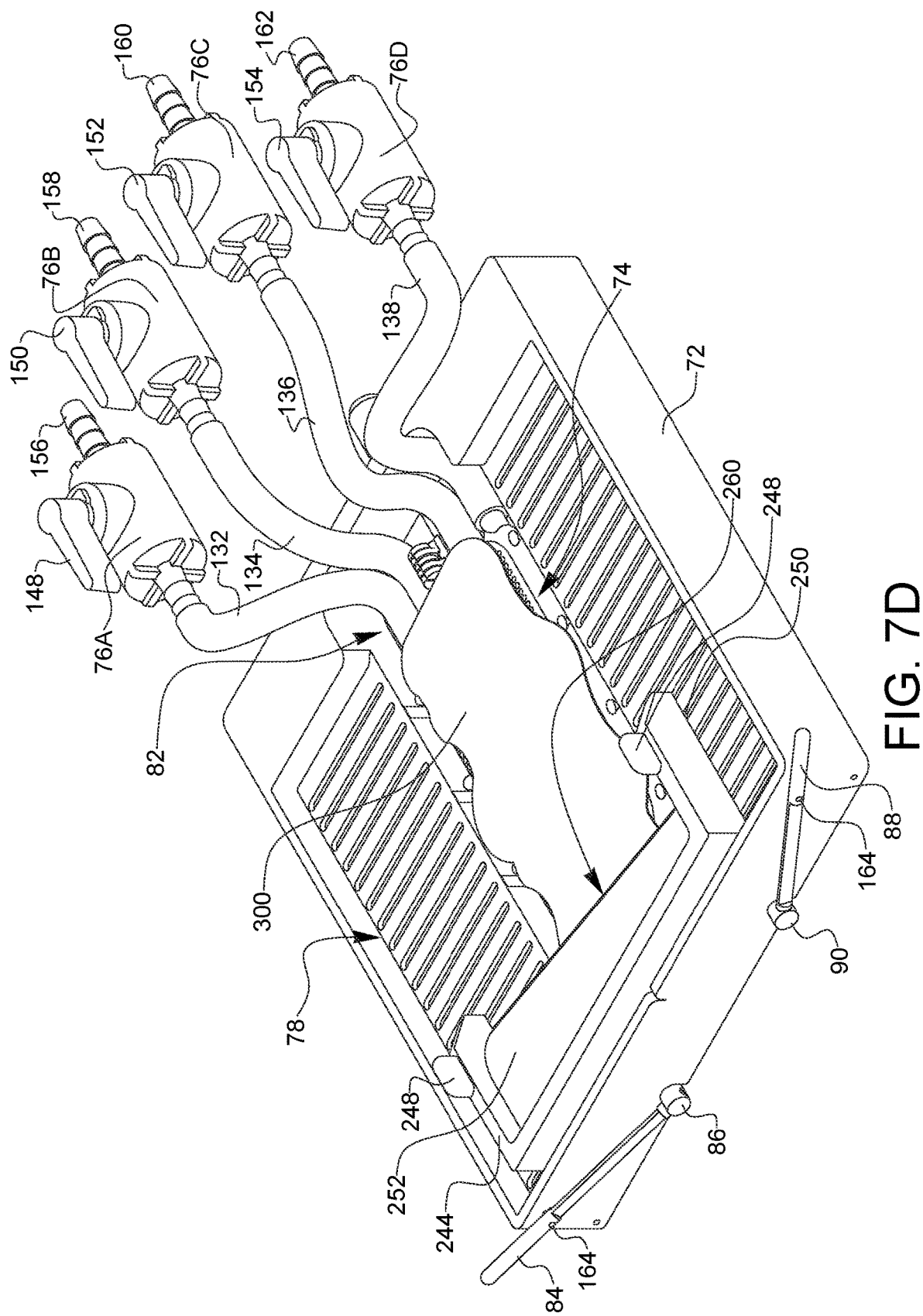
Figure 7E:
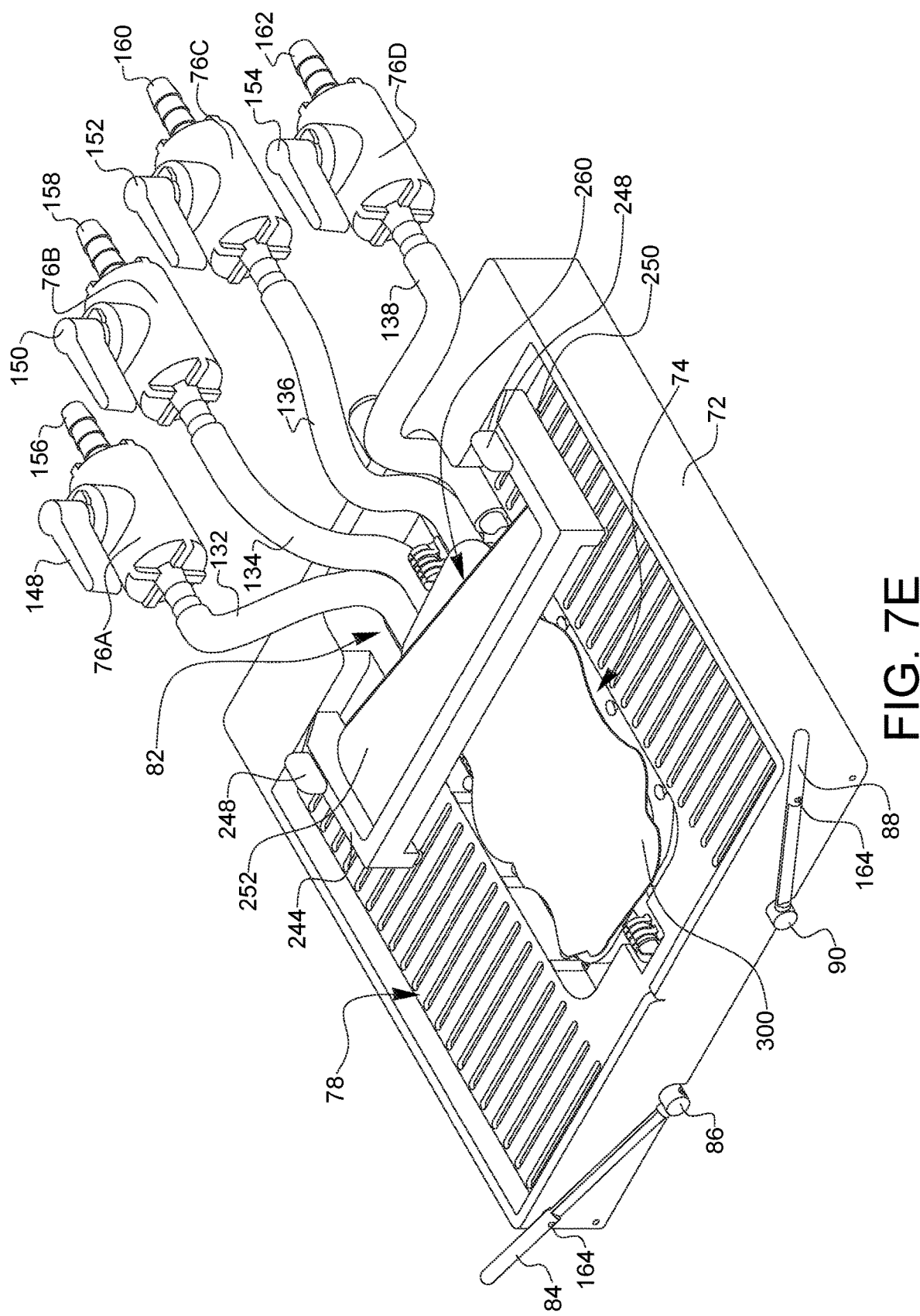

FIG. 7D illustrates an initial placement of the slicing sled 244 onto the deck 72 and into the first fluid reservoir 78. The slicing sled 244 spans the second inner fluid reservoir 82 and is configured to be manually traversed across the pericardial tissue 300 to slice any rough tissue from the top surface, leaving a uniform thickness of resulting pericardial tissue 300. The uniform thickness is dictated by the height of the offsets 250 on either side of the slicing sled 244 that ride within the first fluid reservoir 78 setting the height of the blade edge 260 relative to the surface of the platform 74. A shear action in a zig-zag pattern may be used to trim away any redundant or rough anterior tissue material, leaving behind a layer of pericardial tissue 300 approximately 0.15 inches in thickness. While this slicing sled 244 includes the fixed offsets 250 on either side, alternate embodiments having adjustable offsets or alternate methods of slicing the pericardial tissue 300 to a different uniform thickness may be used as well. Once the slicing sled 244 has been traversed across the pericardial tissue 300, as shown in FIG. 7E, the slicing sled 244 is removed and any loose debris is washed away and removed from the deck 72 of the repair structure apparatus 70.

Figure 7F:
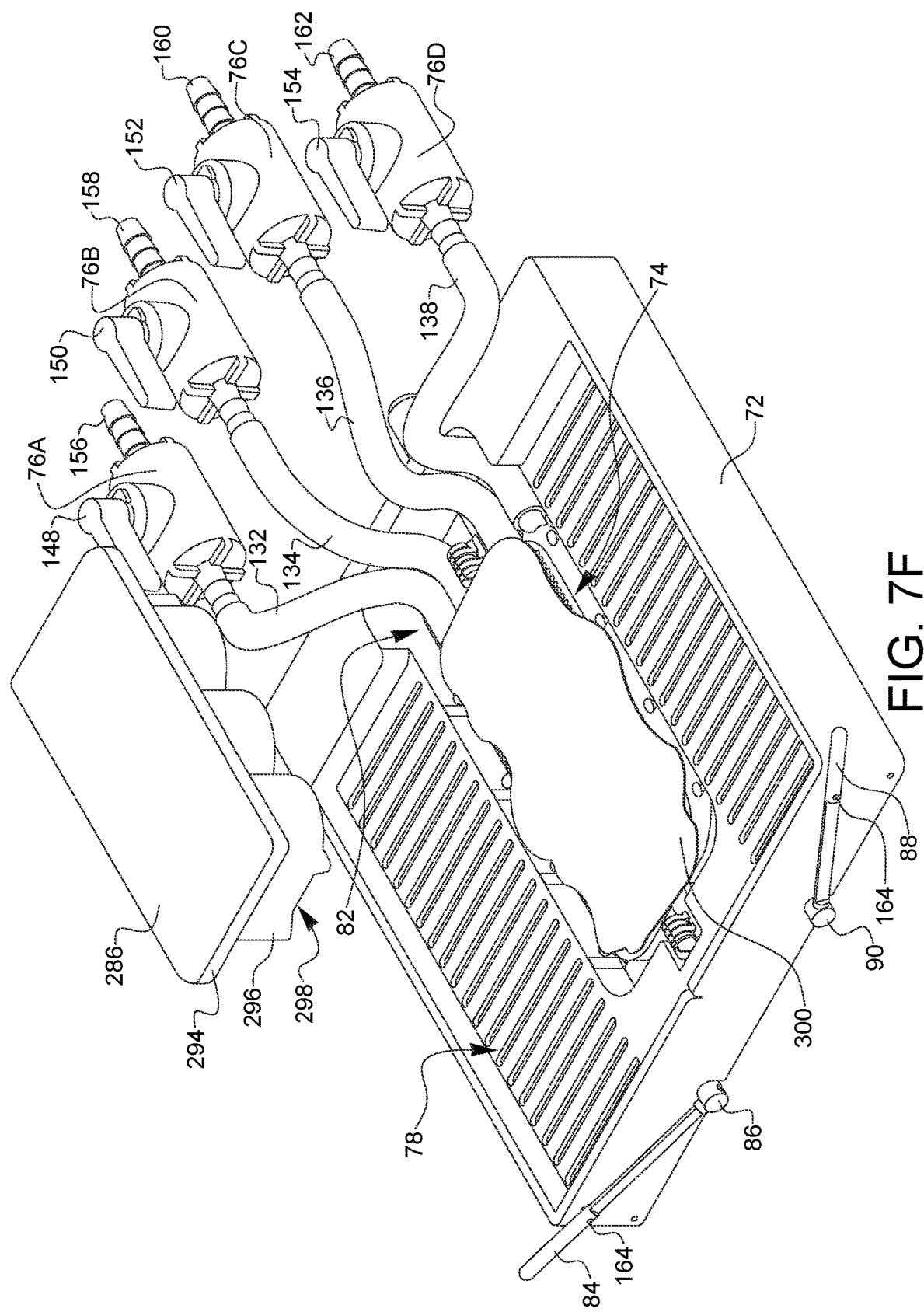
Figure 7G:
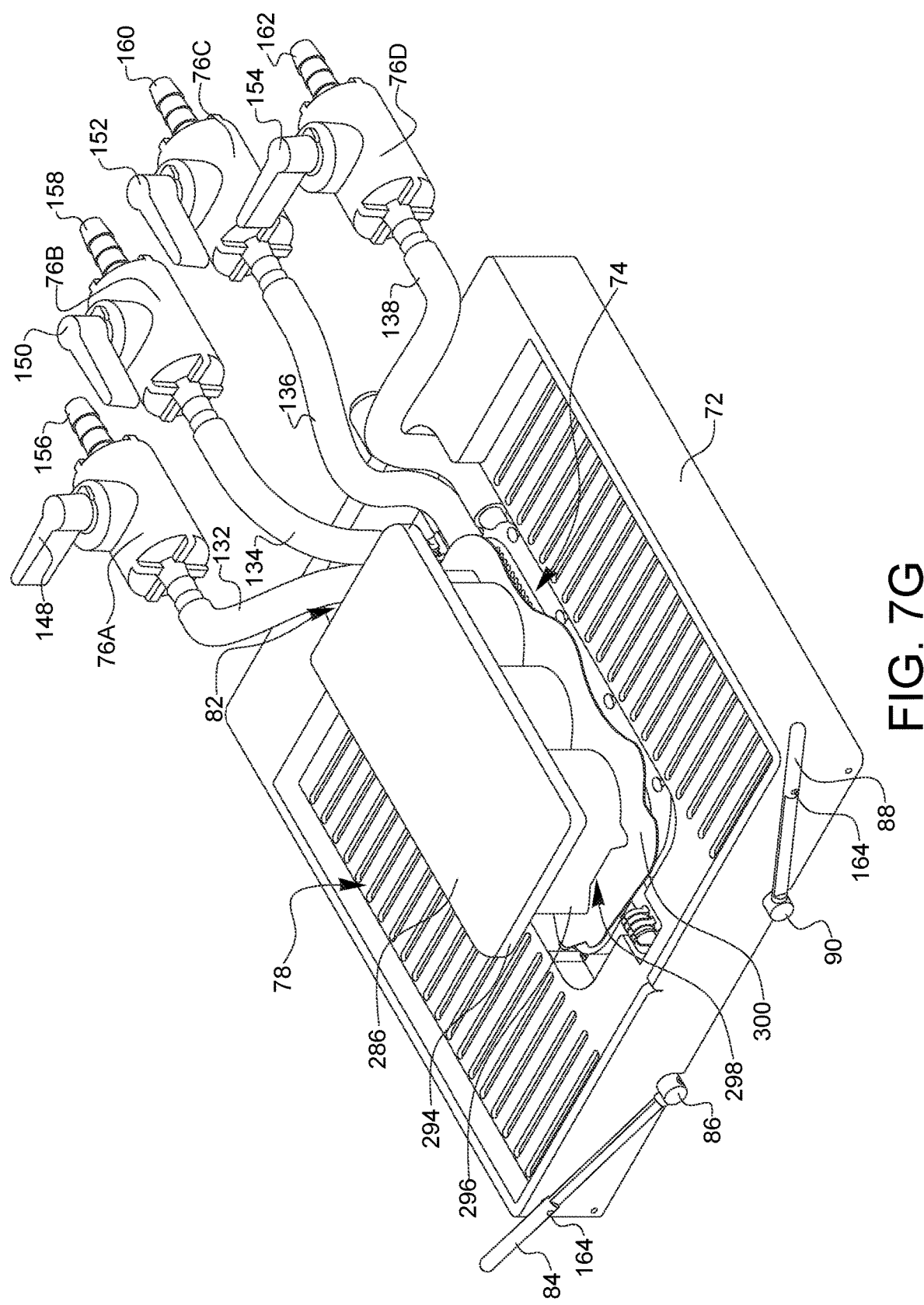
Figure 7H:
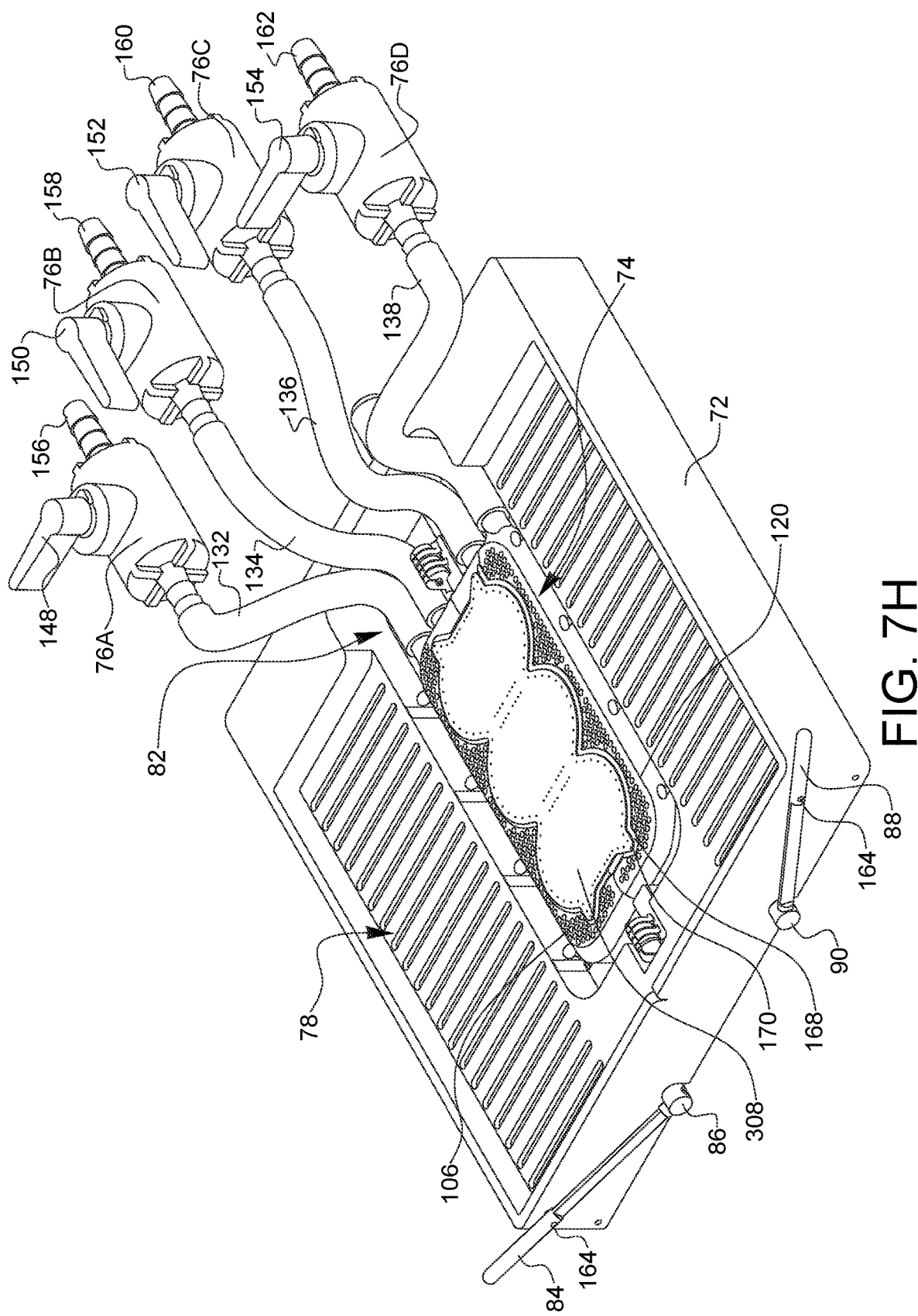

FIG. 7F illustrates the template 286 of FIGS. 6G and 6H being lowered onto the platform 74 with the preserved and prepared pericardial tissue 300 held in place by vacuum through the porous surfaces in the platform 74 of the repair structure apparatus 70. The cutting template 286 resembles a cookie cutter and may be alternately referred to as such. The cutting template 286 is lowered onto the platform 74 and aligned to reference off the alignment edge 168 on the platform 74. The alignment edge 168 is obscured by the pericardial tissue 300 in this view. The cutting template 286 is lowered onto the pericardial tissue 300 as illustrated in FIG. 7G and the double-triple-U shape of the pericardial tissue 300 is cut. As the template 286 is pressed down onto the pericardial tissue 300, first vacuum channel 76A and fourth vacuum channel 76D are turned off as shown by rotating first stopcock 148 and fourth stopcock 154, respectively. FIG. 7H shows the resulting sectioned pericardial tissue template 308 used to complete a cardiac repair structure once any excess peripheral tissue has been removed from the vacuum areas corresponding to first porous surface section 106 and separate fourth platform section 120 and its porous surface around the perimeter of the pericardial tissue template. It should be noted that the pericardial tissue template in this depiction also contains some markings or perforations associated with proposed stitching locations. These would not be present in an actual tissue sample but would be noted as proposed stitching locations for subsequent steps in the procedure to construct a cardiac repair structure as described herein.

Figure 7J:
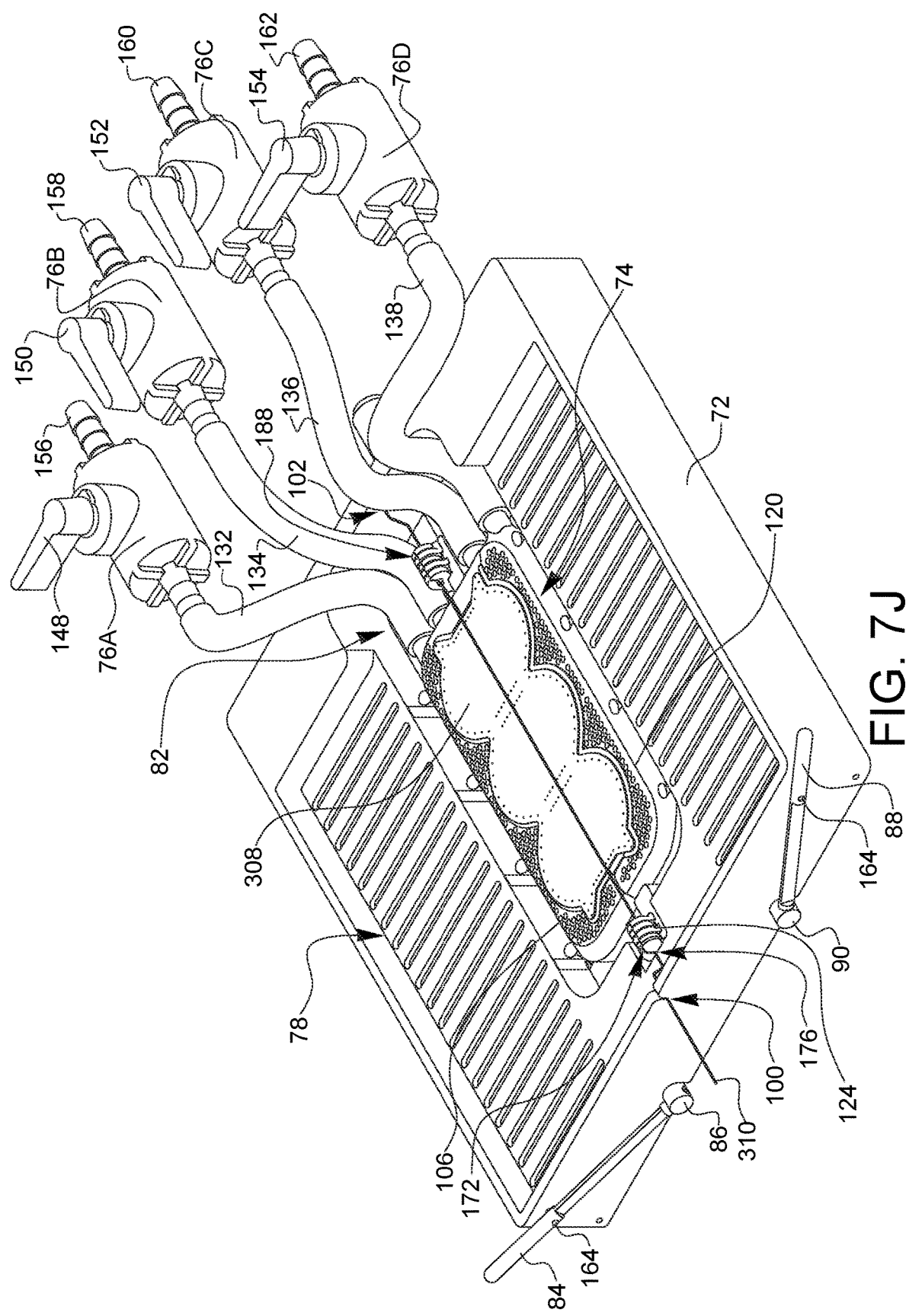
Figure 7K:
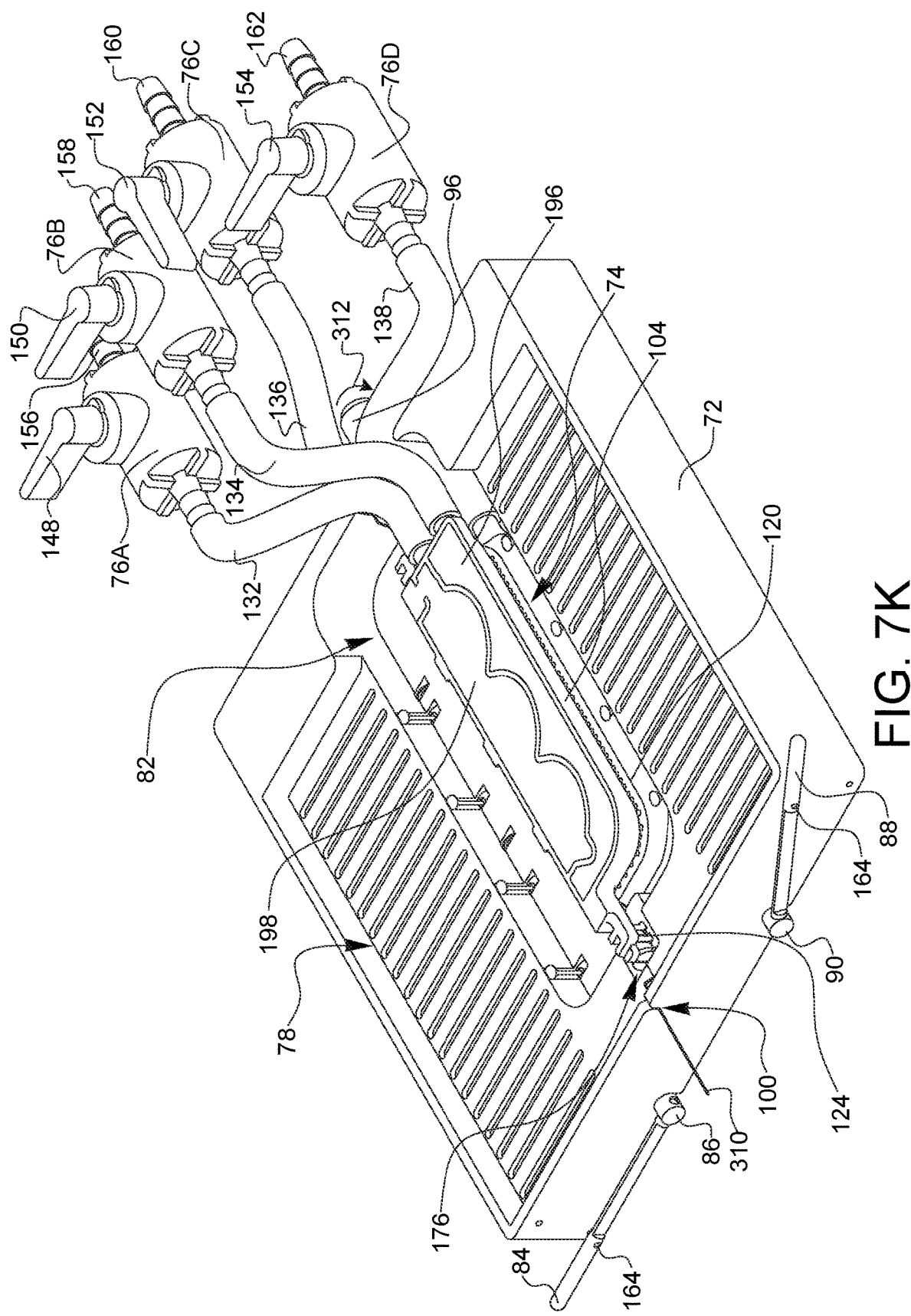
Figure 7L:
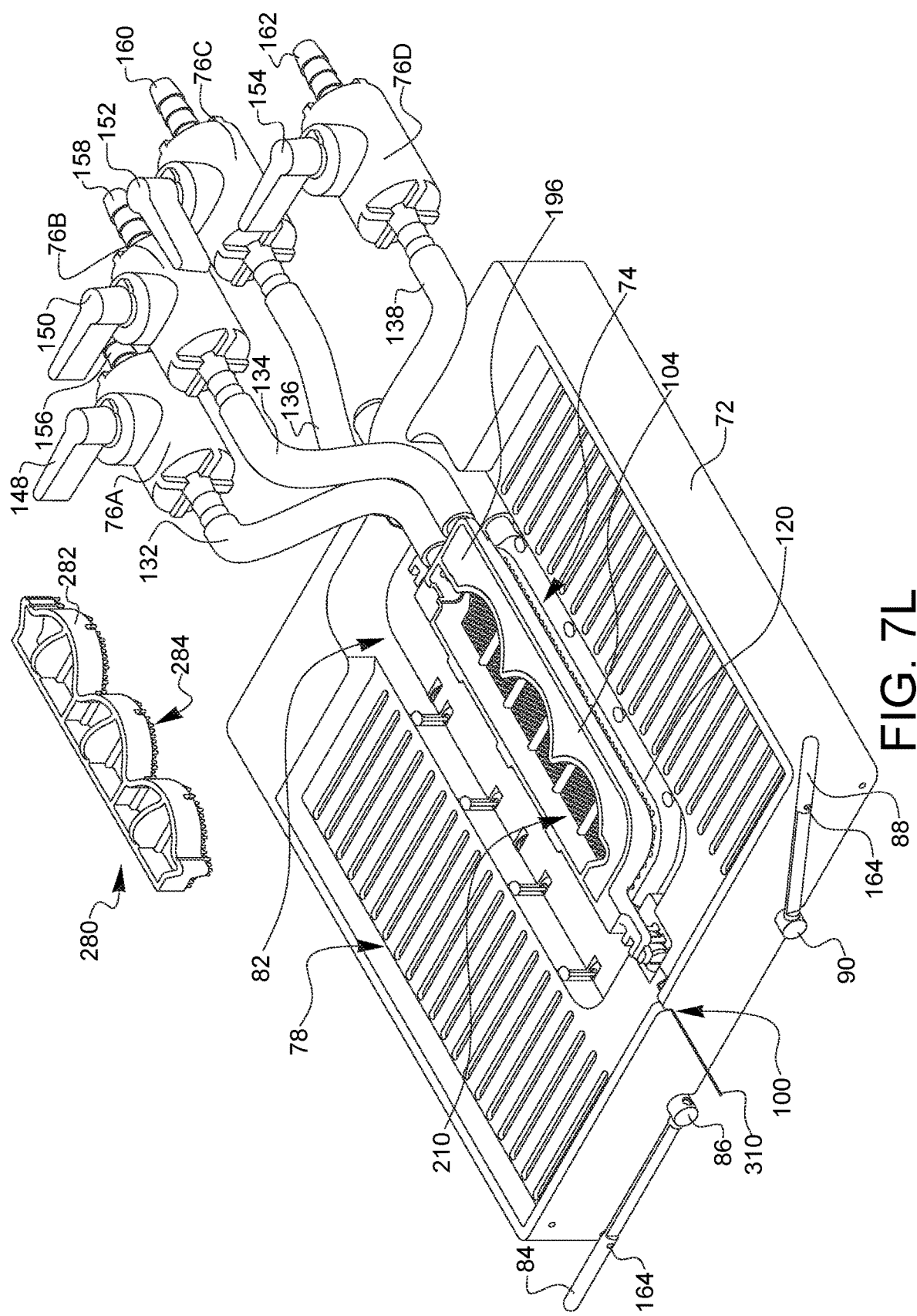
Figure 7N:
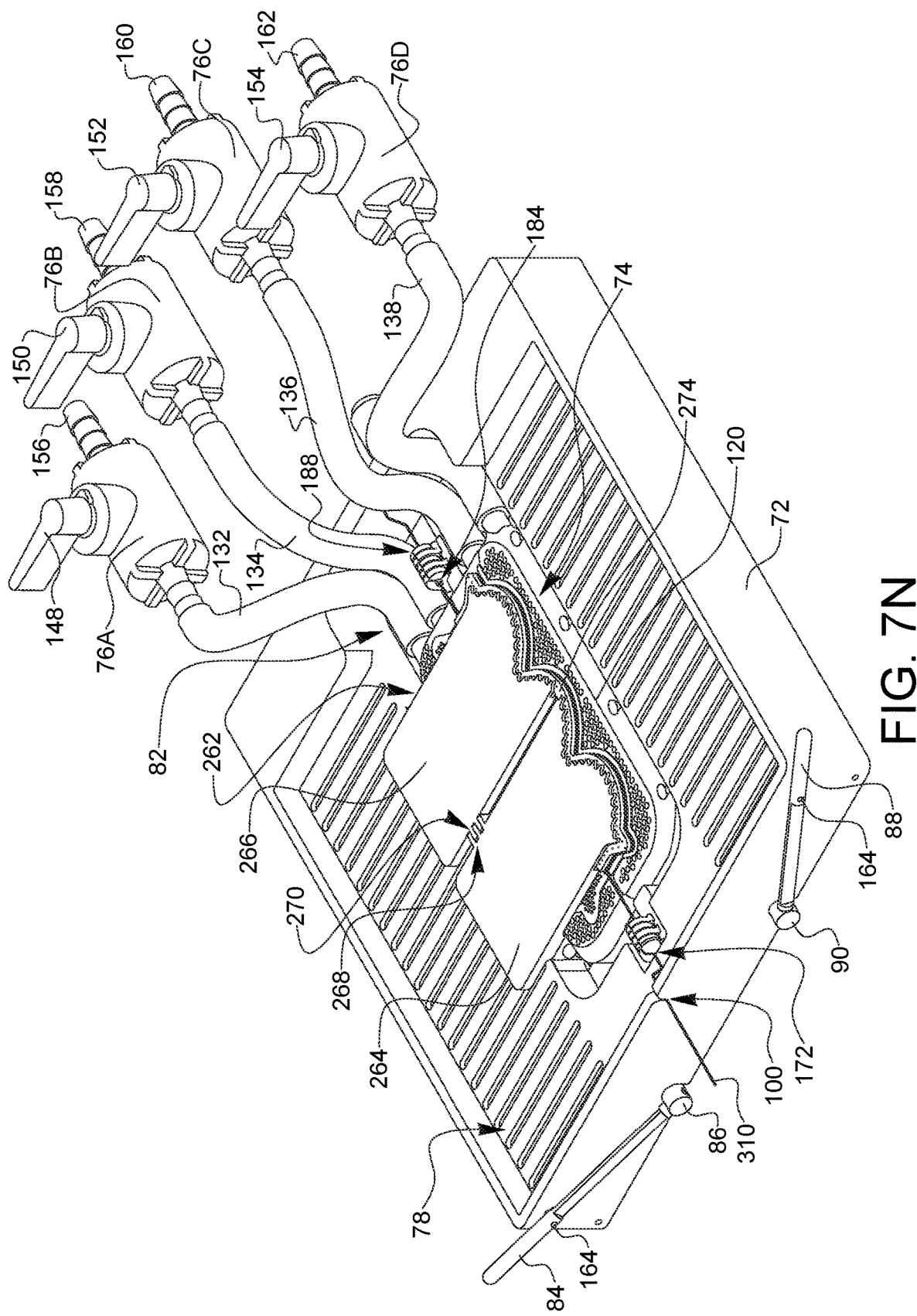
Figure 7P:
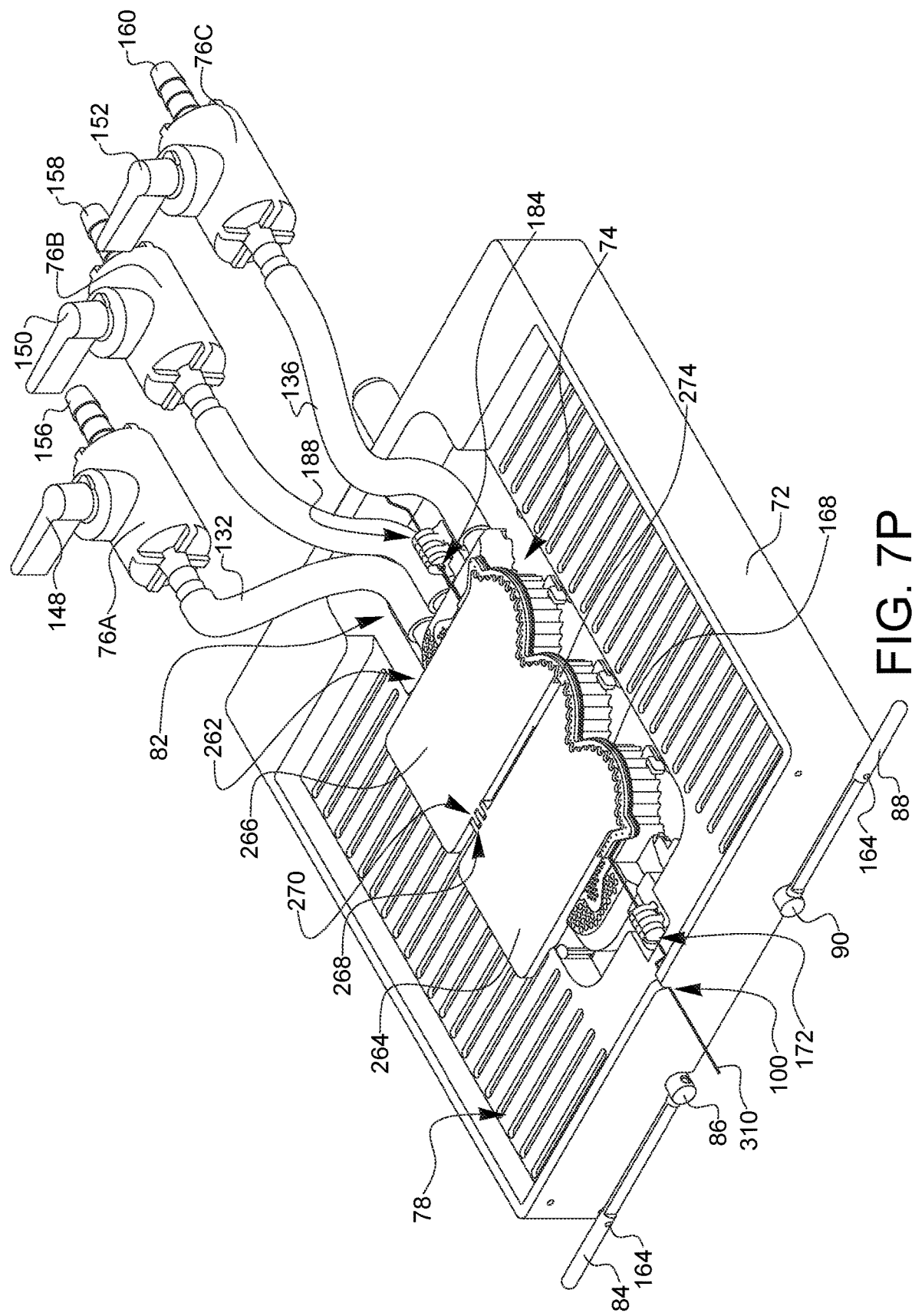
Figure 7Q:
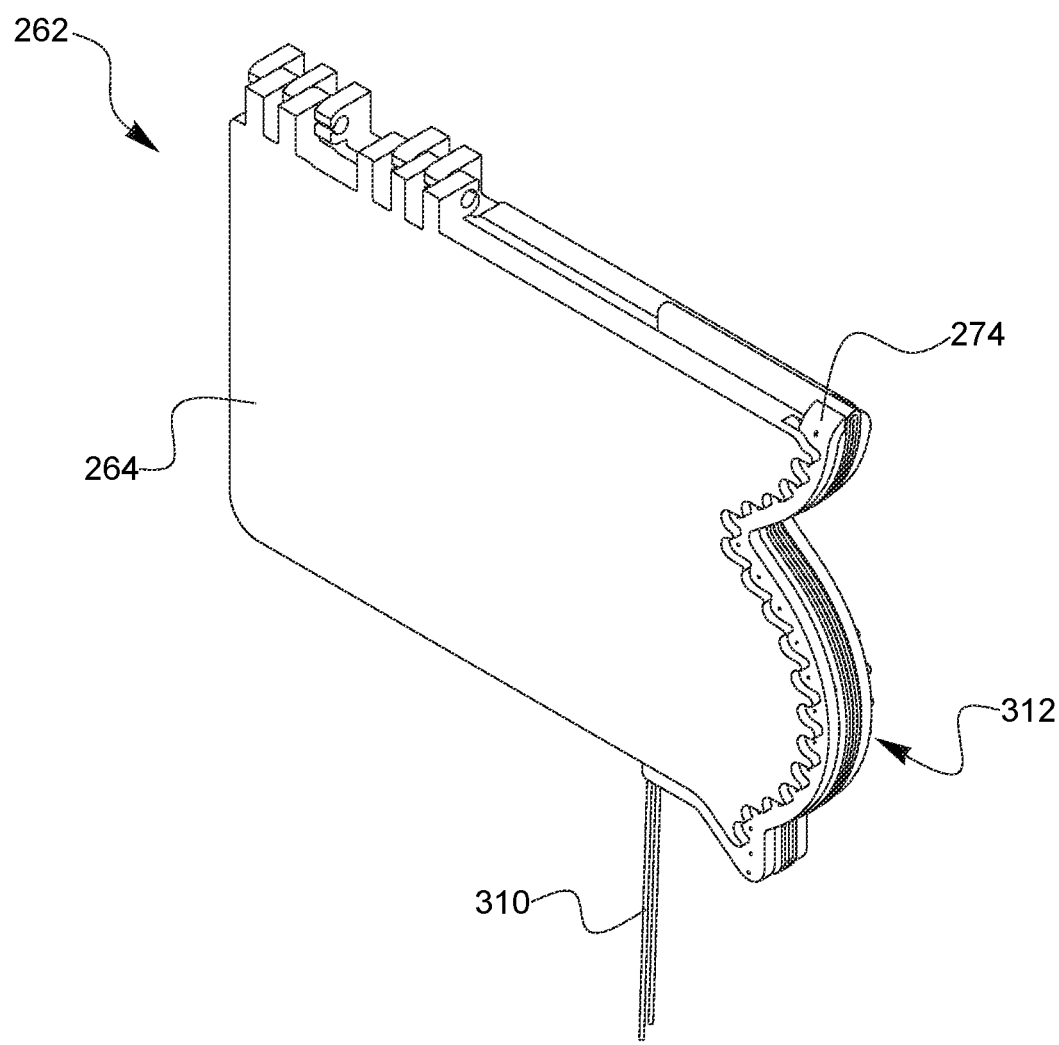

FIG. 7J illustrates a subsequent procedural step in use for the repair structure apparatus of FIG. 4 in constructing a cardiac repair structure or heart valve from autologous pericardial tissue. A strand of double-armed ePTFE suture 310 is placed along the free-edge fold line of the sectioned pericardial tissue template 308 through the first suture channel 100 of the deck 72, into pin path 172 of mushroom-shaped hinge 124, through suture channel 188 of mushroom-shaped hinge 126 and through second suture channel 102 on deck 72 of the repair structure apparatus 70. The suture 310 is secured via conventional means of suture securing known in the art. Once the suture 310 is secured, the first platform half 104 of the platform 74 is rotated 180-degrees towards the second platform half 114, capturing the ePTFE suture within the layers of sectioned pericardial tissue template 308 at the fold line, as illustrated in FIG. 7K. second vacuum channel 76B is then turned off by rotating second stopcock 150 to cut off any vacuum supply to the first platform segment 104 of the platform 74. The sectioned pericardial tissue template 308 can then be mechanically released from the first platform segment 104 of the platform 74 using the pin cushion tool 280 of FIGS. 6E-6F to press through the second chamber 210 through to the porous surface of the second porous surface section 108 once the second lower chamber 198 is removed from the first platform segment 104. While this mechanical release using the pin cushion tool 280 is illustrated in FIG. 7L, the removal of the second lower chamber floor 198 is not shown here. The first platform segment 104 is now rotated back 180-degrees to its initial flat position, leaving the cut and folded pericardial tissue 312 folded over the double-armed ePTFE suture 310. This arrangement is shown in FIG. 7M. FIG. 7N illustrates a subsequent step wherein the folding felt holder 262 of FIGS. 6C and 6D is placed onto the vacuum chamber alignment edge 168 of the third platform segment 116 of the platform 74. Once the folding felt holder 262 is placed on the platform 74, the separate fourth platform segment 120 of the platform 74 can be removed as illustrated in FIG. 7P. The vacuum channels 76D and associated connections are not shown here for the purposes of clarity. With the ePTFE thin felt trim border with the triple-U tissue formation over the annular edge of the tissue layers, the scallops 272 on the edge of the folding felt holder 262 and corresponding vacuum chamber bay features are used as a guide to run a sewing suture from the nadir of the non-coronary sinus to the right side of the left commissural felt. The same suture is then run from the nadir of the left non leaflet to the right commissural felt edge. At this point, vacuum channels 76C may be turned off by actuating third stopcock 152. The folding felt holder 262 can now be removed from the platform with additional assistance of the pin cushion tool 280 as needed. The folding felt holder 262 is then folded in half as shown in FIG. 7Q. At this stage, the other vacuum sources may be removed or at least completely shut off during the completion of the procedure. Also, the platform 74 and any associated instrumentation and devices can be removed.

Completion of the construction of the cardiac repair structure as shown and described in regard to FIG. 1 is accomplished by lifting the sutured double layered valve sutured to the annular felt from the vacuum plate while still attached to the folding felt holder as illustrated in FIG. 7Q. The folding felt holder 262 is folded 180-degrees to align the two contact surfaces for subsequent suturing at the R-L commissural felt. Suturing is continued by suturing at the connection of the R-L commissure felt, and a titanium fastener is attached to construct and fasten the suture ends, tails out. Alternatively, a secondary surgical sewing machine can be used to sew the pleated seam of the L-R commissure felt. It is recommended that the last suture or bite is above the ePTFE strands. The folded felt holder 262 can then be removed. The pleated seam of the R-N commissure felt is then sewed ensuring the last bite is below the ePTFE strands. The pleated seam of the L-N commissure felt is then sewed, ensuring the last bite is below the ePTFE strands. The L-R attachment suture, the R-N attachment suture, and the L-N attachment suture are then placed. Twelve sewing-cuff sutures are placed using a SEWEASY® device, available from www.lsisolutions.com. It should be noted that throughout this process, the viable pericardial tissue is kept moist or submerged in cool physiologic, possibly oxygenated, solution. The autologous heart valve, or autologous cardiac repair structure is now ready to be implanted according to established procedures and the preferred surgical practice of the surgeon and surgical team.

Various advantages of a repair structure for use in minimally invasive cardiac surgery have been discussed above. Embodiments discussed herein have been described by way of example in this specification. It will be apparent to those skilled in the art that the foregoing detailed disclosure is intended to be presented by way of example only, and is not limiting. As just one example, although the end effectors in the discussed examples were often focused on the use of a scope, such systems could be used to position other types of surgical equipment. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A repair structure for cardiac surgery, the repair structure comprising:
   a sheet of harvested pericardial tissue, the sheet comprising:
      a folded edge line that extends from a first end to a second end opposite the first end;
      a first lobe line that extends from a first end to a second end opposite the first end, wherein the first lobe line is parallel to and offset from the folded edge line by a first distance;
      a second lobe line that extends from a first end to a second end opposite the first end, wherein the second lobe line is parallel to and offset from the folded edge line by a second distance;
      a first portion of a first lobe, a first portion of a second lobe, and a first portion of a third lobe, wherein each of the first portion of the first lobe, the first portion of the second lobe, and the first portion of the third lobe is at least partially defined by a corresponding perimeter edge having a shape that is curved, and wherein a starting point and an ending point of the perimeter edge of each of the first portion of the first lobe, the first portion of the second lobe, and the first portion of the third lobe is on or adjacent to the first lobe line;
      a second portion of the first lobe, a second portion of the second lobe, and a second portion of the third lobe, wherein each of the second portion of the first lobe, the second portion of the second lobe, and the second portion of the third lobe is at least partially defined by a corresponding perimeter edge having a shape that is curved, and wherein a starting point and an ending point of the perimeter edge of each of the second portion of the first lobe, the second portion of the second lobe, and the second portion of the third lobe is on or adjacent to the second lobe line;
      a first transverse fold line that extends from a first end disposed at or adjacent to the first lobe line to a second end disposed at or adjacent to the second lobe line, the first end of the first transverse fold line is at or adjacent to the ending point of the perimeter edge of the first portion of the first lobe, and the second end of the first transverse fold line is at or adjacent to the ending point of the perimeter edge of the second portion of the first lobe; and
      a second transverse fold line that extends from a first end disposed at or adjacent to the first lobe line to a second end disposed at or adjacent to the second lobe line, the first end of the second transverse fold line is at or adjacent to the ending point of the perimeter edge of the first portion of the second lobe, and the second end of the second transverse fold line is at or adjacent to the ending point of the perimeter edge of the second portion of the second lobe, wherein the first transverse fold line is offset from the first transverse fold line, wherein the sheet is folded about the folded edge line such that the first lobe line is aligned with the second lobe line and the perimeter edge of the first portion of the first lobe is aligned with the perimeter edge of the second portion of the first lobe, the perimeter edge of the first portion of the second lobe is aligned with the perimeter edge of the second portion of the second lobe, and the perimeter edge of the first portion of the third lobe is aligned with the perimeter edge of the second portion of the third lobe, wherein the first portion of the first lobe and the second portion of the first lobe are folded about the first lobe line and the second lobe line, respectively, to form the first lobe, wherein the first portion of the second lobe and the second portion of the second lobe are folded about the first lobe line and the second lobe line, respectively, to form the second lobe, and wherein the first portion of the third lobe and the second portion of the third lobe are folded about the first lobe line and the second lobe line, respectively, to form the third lobe, wherein the sheet is folded about the first transverse fold line and the second transverse fold line such that the first end of the first lobe line is disposed at or adjacent to the second end of the first lobe line and the first end of the second lobe line is disposed at or adjacent to the second end of the second lobe line such that:

a first side wall is partially defined by the first transverse fold line, a first portion of the first lobe line, and a first portion of the folded edge line, a second side wall is partially defined by the first transverse fold line, the second transverse fold line, a second portion of the first lobe line, and a second portion of the folded edge line, and a third side wall is partially defined by the second transverse fold line, a third portion of the first lobe line, and a third portion of the folded edge line, and wherein a top perimeter edge of each of the first side wall, the second side wall, and the third side wall cooperate to form a triangular shape.

2. The repair structure of claim 1, wherein the first portion of the first lobe and the second portion of the first lobe are symmetrical about the folded edge line, wherein the first portion of the second lobe and the second portion of the second lobe are symmetrical about the folded edge line, and wherein the first portion of the third lobe and the second portion of the third lobe are symmetrical about the folded edge line.

3. The repair structure of claim 1, wherein the starting point of the perimeter edge of the first portion of the first lobe is disposed at the first end of the first lobe line and the ending point of the perimeter edge of the first portion of the third lobe is disposed at the second end of the first lobe line.

4. The repair structure of claim 1, wherein the starting point of the perimeter edge of the second portion of the first lobe is disposed at the first end of the second lobe line and the ending point of the perimeter edge of the second portion of the third lobe is disposed at the second end of the second lobe line.

5. The repair structure of claim 1, wherein the first distance is equal to the second distance.

6. The repair structure of claim 1, wherein the shape of the perimeter edge of each of the first portion of the first lobe, the second portion of the first lobe, the first portion of the second lobe, the second portion of the second lobe, the first portion of the third lobe, and the second portion of the third lobe is identical.

7. The repair structure of claim 1, wherein the shape of the perimeter edge of each of the first portion of the first lobe, the second portion of the first lobe, the first portion of the second lobe, the second portion of the second lobe, the first portion of the third lobe, and the second portion of the third lobe is a segment of a circle.

8. The repair structure of claim 7, wherein the shape of the perimeter edge of each of the first portion of the first lobe, the second portion of the first lobe, the first portion of the second lobe, the second portion of the second lobe, the first portion of the third lobe, and the second portion of the third lobe is a semi-circle.

9. The repair structure of claim 1, wherein the starting point and the ending point of the perimeter edge of each of the first portion of the first lobe, the first portion of the second lobe, and the first portion of the third lobe intersects the first lobe line, and wherein the starting point and the ending point of the perimeter edge of each of the second portion of the first lobe, the second portion of the second lobe, and the second portion of the third lobe intersects the second lobe line.

10. The repair structure of claim 1, wherein each of the first transverse fold line and the second transverse fold line extends normal to the folding edge line.

11. The repair structure of claim 1, wherein each of the top perimeter edges of each of the first side wall, the second side wall, and the third side wall are non-linear.

12. A method of folding a sheet of harvested pericardial tissue to create a repair structure for cardiac surgery, the sheet comprising: a folded edge line that extends from a first end to a second end opposite the first end; a first lobe line that extends from a first end to a second end opposite the first end, wherein the first lobe line is parallel to and offset from the folded edge line by a first distance; a second lobe line that extends from a first end to a second end opposite the first end, wherein the second lobe line is parallel to and offset from the folded edge line by a second distance; a first portion of a first lobe, a first portion of a second lobe, and a first portion of a third lobe, wherein each of the first portion of the first lobe, the first portion of the second lobe, and the first portion of the third lobe is at least partially defined by a perimeter edge having a shape that is curved, and wherein a starting point and an ending point of the perimeter edge of each of the first portion of the first lobe, the first portion of the second lobe, and the first portion of the third lobe intersects the first lobe line; and a second portion of the first lobe, a second portion of the second lobe, and a second portion of the third lobe, wherein each of the second portion of the first lobe, the second portion of the second lobe, and the second portion of the third lobe is at least partially defined by a perimeter edge having a shape that is curved, and wherein a starting point and an ending point of the perimeter edge of each of the second portion of the first lobe, the second portion of the second lobe, and the second portion of the third lobe intersects the second lobe line, the method comprising:

folding the sheet about the folded edge line such that the first lobe line is aligned with the second lobe line and the perimeter edge of the first portion of the first lobe is aligned with the perimeter edge of the second portion of the first lobe, the perimeter edge of the first portion of the second lobe is aligned with the perimeter edge of the second portion of the second lobe, and the perimeter edge of the first portion of the third lobe is aligned with the perimeter edge of the second portion of the third lobe;

folding the first portion of the first lobe and the second portion of the first lobe about the first lobe line and the second lobe line, respectively, to form the first lobe;

folding the first portion of the second lobe and the second portion of the second lobe about the first lobe line and the second lobe line, respectively, to form the second lobe;

folding the first portion of the third lobe and the second portion of the third lobe about the first lobe line and the second lobe line, respectively, to form the third lobe.

13. The method of claim 12, the sheet further comprising:
a first transverse fold line that extends from a first end to a second end opposite the first end, wherein the first transverse fold line extends between the first lobe line and the second lobe line, the first end of the first transverse fold line is at or adjacent to the first lobe line, the second end of the first transverse fold line is at or adjacent to the second lobe line, the first end of the first transverse fold line is at or adjacent to the ending point of the perimeter edge of the first portion of the first lobe, and the second end of the first transverse fold line is at or adjacent to the ending point of the perimeter edge of the second portion of the first lobe; and a second transverse fold line that extends from a first end to a second end opposite the first end, wherein the second transverse fold line extends between the first lobe line and the second lobe line, the first end of the second transverse fold line is at or adjacent to the first lobe line, the second end of the second transverse fold line is at or adjacent to the second lobe line, the first end of the second transverse fold line is at or adjacent to the ending point of the perimeter edge of the first portion of the second lobe, and the second end of the second transverse fold line is at or adjacent to the ending point of the perimeter edge of the second portion of the second lobe, the method further comprising:
folding the sheet about the first transverse fold line and the second transverse fold line such that the first end of the first lobe line is disposed at or adjacent to the second end of the first lobe line and the first end of the second lobe line is disposed at or adjacent to the second end of the second lobe.

* * * * *